United States Patent [19]
Haynes

[11] Patent Number: 5,091,188
[45] Date of Patent: Feb. 25, 1992

[54] PHOSPHOLIPID-COATED MICROCRYSTALS: INJECTABLE FORMULATIONS OF WATER-INSOLUBLE DRUGS

[76] Inventor: Duncan H. Haynes, 4051 Barbarossa Ave., Miami, Fla. 33133

[21] Appl. No.: 514,012

[22] Filed: Apr. 26, 1990

[51] Int. Cl.⁵ .................... A61K 37/22; A61F 13/00
[52] U.S. Cl. .................................. 424/450; 424/422; 424/405; 424/408; 424/409
[58] Field of Search ............... 424/450, 422, 405, 408, 424/409

[56] References Cited

U.S. PATENT DOCUMENTS

| | | | |
|---|---|---|---|
| 4,298,594 | 11/1981 | Sears et al. | 424/19 |
| 4,309,421 | 1/1982 | Ghyczy et al. | 424/19 |
| 4,331,654 | 5/1982 | Morris | 424/14 |
| 4,332,795 | 6/1982 | Ghyczy et al. | 424/199 |
| 4,332,796 | 6/1982 | Los | 424/229 |
| 4,345,588 | 8/1982 | Widder et al. | 128/1.3 |
| 4,378,354 | 5/1983 | Ghyczy et al. | 424/199 |
| 4,411,894 | 10/1983 | Schrank | 424/199 |
| 4,421,747 | 12/1983 | Ghyczy et al. | 424/199 |
| 4,492,720 | 1/1985 | Mosier | 427/213.3 |
| 4,761,288 | 8/1988 | Mezei | 424/450 |
| 4,839,111 | 6/1989 | Huang | 264/4.6 |
| 4,973,465 | 11/1990 | Baurain et al. | 424/406 |

FOREIGN PATENT DOCUMENTS 8500011 1/1985 PCT Int'l Appl. .

Primary Examiner—Thurman K. Page
Assistant Examiner—G. S. Kishore
Attorney, Agent, or Firm—Nixon & Vanderhye

[57] ABSTRACT

Water-insoluble drugs are rendered injectable by formulation as aqueous suspensions of phospholipid-coated microcrystals. The crystalline drug is reduced to 50 nm to 10 μm dimensions by sonication or other processes inducing high shear in the presence of phospholipid or other membrane-forming amphipathic lipid. The membrane-forming lipid stabilizes the microcrystal by both hydrophobic and hydrophilic interactions, coating and enveloping it and thus protecting it from coalescence, and rendering the drug substance in solid form less irritating to tissue. Additional protection against coalescence is obtained by a secondary coating by additional membrane-forming lipid in vesicular form associated with and surrounding but not enveloping the lipid-encapsulated drug particles. Tissue-compatible formulations containing drug in concentrations up to 40% (w/v) are described. The preparations can be injected intra-lesionally and in numerous other sites, including intra-venous, intra-arterial, intra-muscular, intra-dermal, etc. The disclosure describes examples of formulations and pharmacokinetic data with antibiotics, anthelmintic drugs, anti-inflammatory drugs, local and general anesthetics, and biologicals.

18 Claims, 9 Drawing Sheets

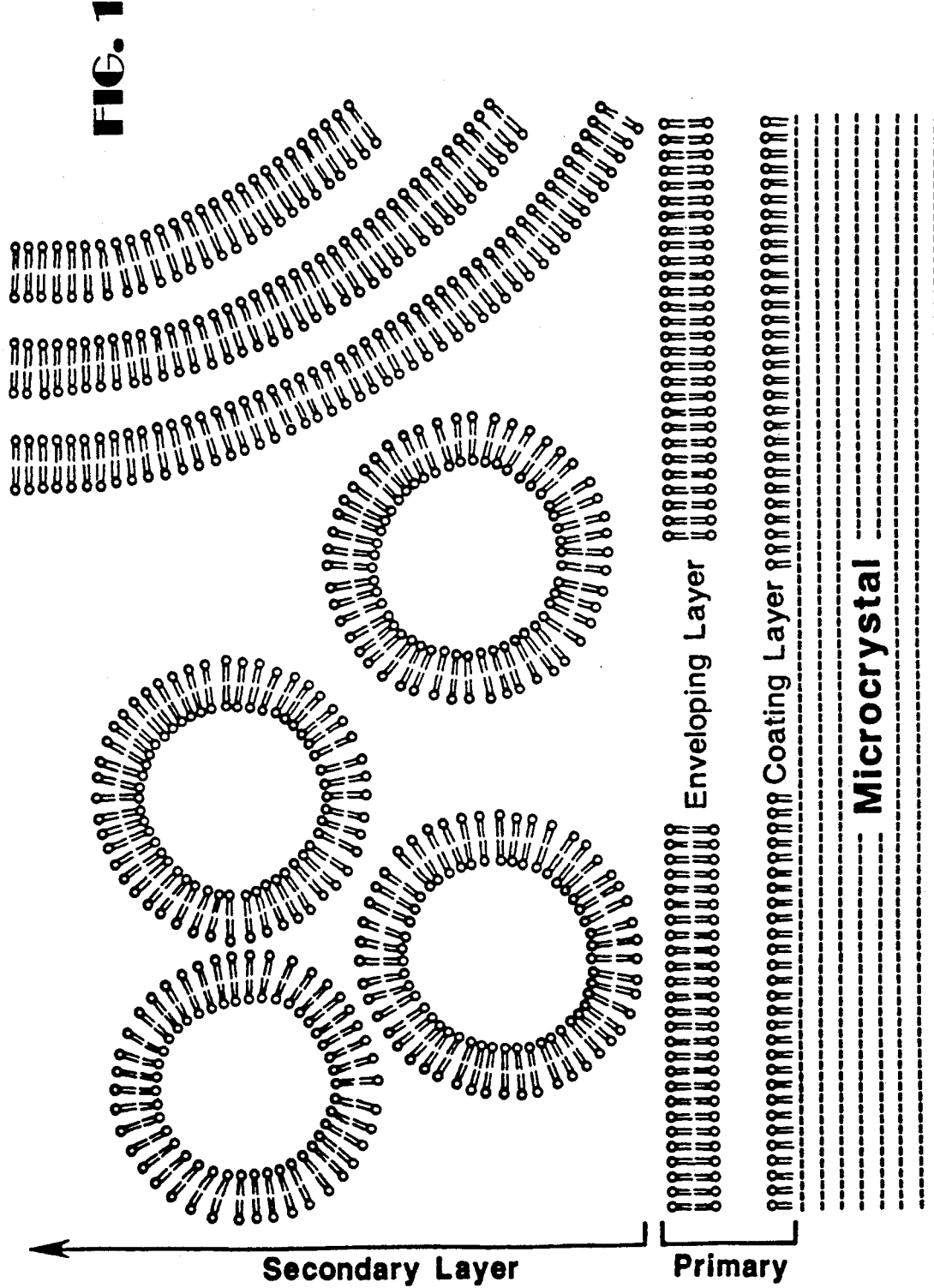

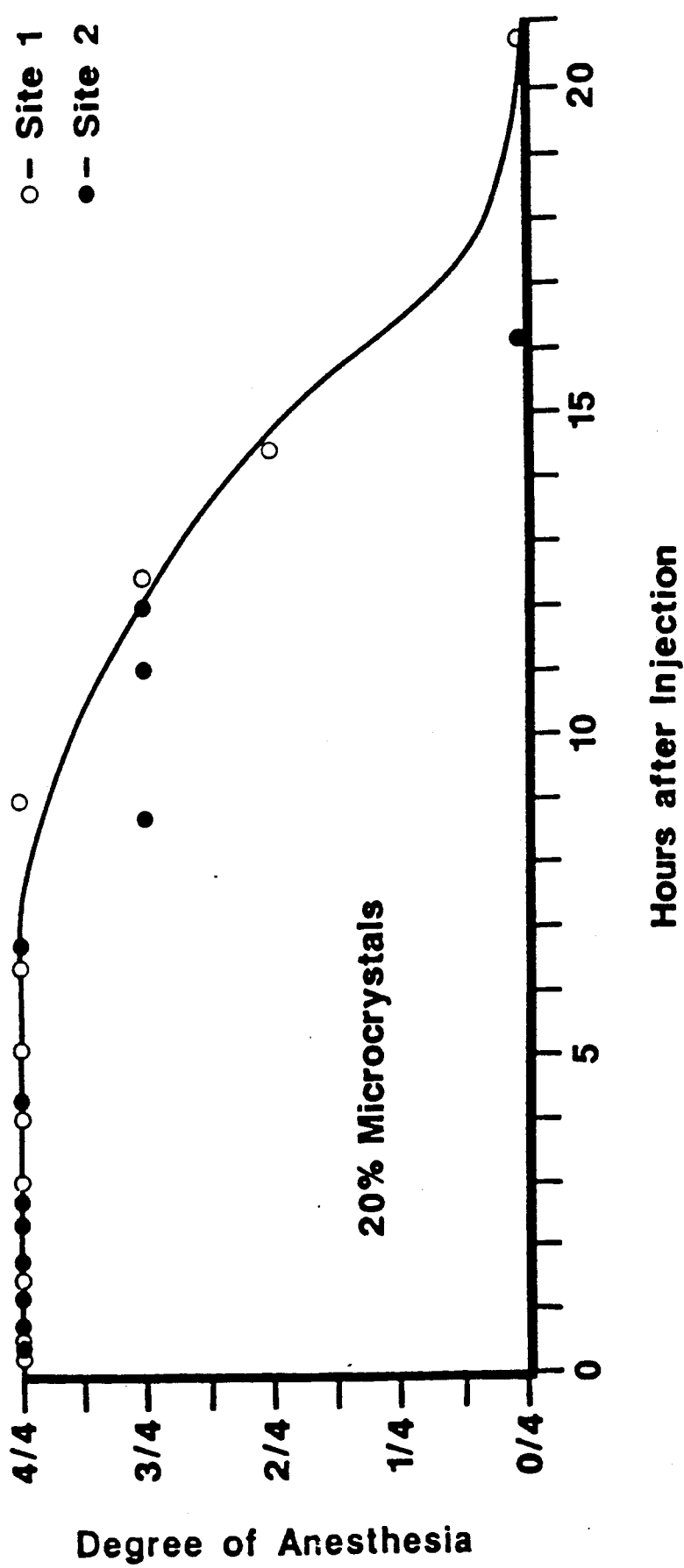

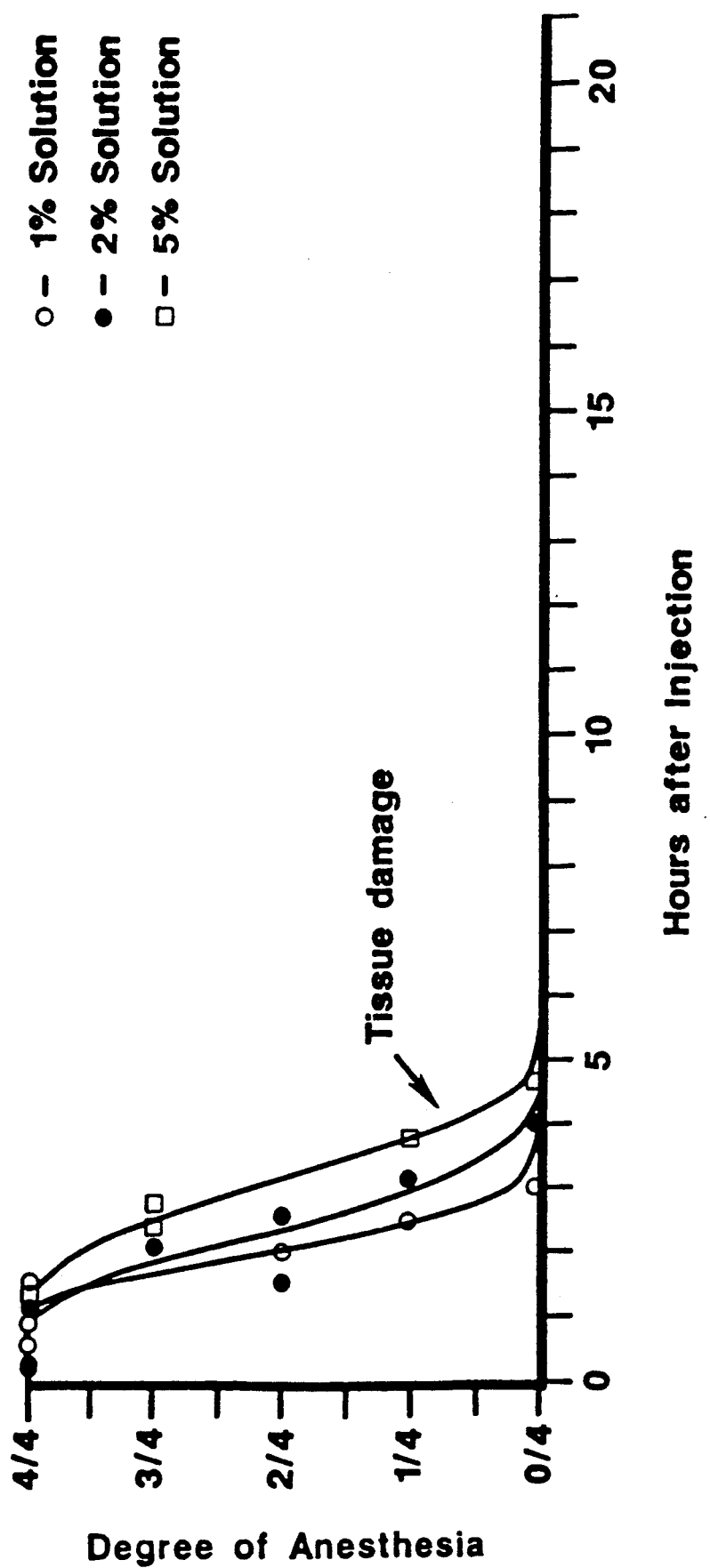

PHOSPHOLIPID-COATED MICROCRYSTALS: INJECTABLE FORMULATIONS OF WATER-INSOLUBLE DRUGS

This invention relates to an injectable delivery form enabling the injection of high concentrations of water-insoluble drugs into a mammalian host and affording sustained release of the injected drug. The present invention shows that crystalline water-insoluble drugs can be reduced to submicron dimensions and suspended in aqueous media at high concentration in a pharmaceutically elegant injectable form by coating with a membrane-forming lipid. The coating is generally a phospholipid but can be made from any membrane-forming lipid. The microcrystal is coated by a layer of membrane-forming lipid which stabilizes the microcrystal by both hydrophobic and hydrophilic interaction. The fatty acyl chains of the phospholipid stabilize the microcrystal by hydrophobic interaction and the polar head groups of the phospholipid stabilize the coated-microcrystal through their interaction with solvent water. The coated microcrystal can be further stabilized by envelopment by the lipid in bilayer form, and by the inclusion of excess membrane-forming lipid in the suspending medium in the form of vesicles. The preparation is tissue-compatible and gives sustained release upon intra-muscular (IM), subcutaneous (Sub-Q), intradermal injection or injections into other confined tissues or spaces (intra-peritoneal, intra-articular, epidural, etc.). The preparation is capable of giving rapid release when injected into the blood, a large and less confined compartment in which it experiences rapid dilution. The preparation can be injected intra-lesionally to produce high local doses without involving the rest of the system. The invention is distinguished from existing drug delivery systems by its injectability, its tissue-compatibility, its small particle size, its high payload, its syringability and stability in storage, its use of phospholipid as the sole coating material, and its non-antigenicity.

BACKGROUND OF INVENTION

Water-soluble drugs are readily injectable. Water-insoluble drugs are not. For water-insoluble (or oil-soluble) drugs the creation of injectable forms represents a substantial problem. The Pharmacopea contains many examples of water-insoluble drugs which must be taken orally because no adequate injectable form exists for them. Present art is limited in terms of the drug concentration and total volume which can be injected. Its application is limited by problems of local irritation, tissue destruction, etc. (in IM injection) and thrombophlebitis, thromboembolism, pulmonary capillary blockage, etc. (in IV injection).

As a preliminary to discussing prior art, it is useful to consider the criteria required of injectable preparations. The following criteria can be extracted from current clinical practice and from general guidelines used by the U.S. Food and Drug Administration in licensing new injectable products.

A. The preparation and its vehicle must be tissue-compatible: This requirement is equally important for injection into tissues and into the circulation. Injection of a deleterious agent into muscle can cause pain, irritation, tissue destruction, cellular reactions, fibrosis or purulent reactions. Injection of a deleterious agent into the circulation can result in thrombophlebitis, including damage to the artery or vein, clot formation in the artery or vein and blockage of the circulation to the tissue or the lungs. As described below, solubilization strategies involving the use of organic solvents, extreme pH and detergents are severely limited by these problems.

B. The formulation must not contain particles of diameter $>10$ um: Particles with dimensions greater than 10 um will block blood capillaries. If administered intra-arterially (IA), they will lodge in the capillaries of the tissue, causing local ischemia. If administered IV, they will lodge in the lung capillaries and cause respiratory distress. For reasons of safety, the $<10$ um criterion must be met for other intended routes of injection (e.g., intra-muscular, IM) due to the danger of inadvertent IV or IA injection. As described below, most of the controlled release technology directed at oral dosing is inapplicable to injectable forms because it fails to meet this criterion.

C. The formulation must allow injection of sufficient quantities of drug: The formulation must carry the drug at high concentration. As an example, if the highest concentration available for a drug is 2% (w/v) or 20 mg/ml and the largest practical volume for an IM injection into man is 5 ml, then a single injection can supply only 100 mg of the drug. If the drug is sufficiently potent, this will present no problem. However, there are many examples in which 1-2 gm of drug must be introduced into the body. This would require either a 10- or 20-fold larger volume (impractical or impossible) or 10-20 times the concentration (heretofore unachievable).

D. The formulation must not rely on constituents which may elicit an allergic response: This is a particular problem for injections into the skin and muscle. Repeated injections of foreign proteins or macromolecules can elicit an immune response. Much of the present art in controlled release relies on "plastics", cross-linked serum albumin, or polymers such as poly (D,L) lactic acid.

E. To be generally useful, the delivery system must have a high "payload": Payload can be defined as the ratio of weight drug delivered to weight of carrier, or encapsulating substance. For example, if a delivery system uses 10 gm of wax or polymer to encapsulate 2 gm of drug, then its payload is 0.2. Delivery systems with low payload will require large amounts of encapsulating substance. The ability of the tissue or vascular compartment to metabolize or remove this substance, however benign, will limit the amount of drug which can be given.

F. The formulation must be stable, grossly homogeneous, syringable and pharmaceutically elegant and must maintain these properties for a reasonable shelf life: The phospholipid-coated microcrystal disclosed in this specification is unique in that it satisfies all of these criteria. It is also unique in that, while satisfying the above criteria, it enables water-insoluble drugs to be injected at high concentrations as high as 40% (w/v).

PRIOR ART

Prior art can be considered in terms of both current pharmaceutical and clinical practice, and in terms of the patent and scientific literature. The survey below shows that none of the existing systems fulfills all of the 6 criteria described above for an injectable form of a water-insoluble drug.

COMMERCIALLY-AVAILABLE FORMS

Medications falling into this category can be definitively surveyed by reference to the Physicians' Desk Reference (PDR, from Medical Economics Company, Inc., Oradell, N.J.) which describes all licensed products in the U.S. One approach to the problem is to render the drug water-soluble by ionizing it using non-physiological pH. As an example, thiopental is supplied as a sodium salt, which upon addition of sterile water, makes an alkaline solution of the drug at 0.2–5% which can be IV-injected. Listed adverse reactions include venous thrombosis or phlebitis extending from the site of injection (Abbott, 1988 PDR, p. 556–559).

Another approach, applicable to IM injection only, has been to inject a solution of compound in vegetable oil. Although the triglycerides in vegetable oil are tissue compatible, bulk oil is not readily absorbed or metabolized by the body. Oil boluses become "walled off" by growth of encapsulation tissue and can persist for months. Due to problems with oil granuloma and serious risks associated with inadvertent IV or IA injection, this approach is largely superseded. A remaining example is a 7.05% solution of haloperidol decanoate in sesame oil (McNeil, PDR, pp. 1240–1241).

Another approach to the problem is to solublize the drug in an organic solvent. As an example, diazepam (Valium ®) is solublized to a concentration of 5 mg/ml (0.5%) in a solution of 40% propylene glycol, 10% ethyl alcohol, water and preservatives. For IV use, warnings are given to reduce the possibility of venous thrombosis, phlebitis, local irritation, etc. which are reported under adverse reaction. The preparation is not stable to dilution in water (Roche, 1988 PDR, pp. 1764–1766.

Due to local reactions of organic solvents, their human use is fairly restricted. This is not the case in veterinary use in food animals in which high drug concentrations are required due to the volume limitations of the syringe (20 ml) and other practical considerations. An example is a commercial 10% (w/v) alkalinized solution of oxytetracycline in propylene glycol for IM injection in cattle. This produces pain on injection and local damage.

A different approach is to solublize or suspend the drug with non-ionic detergent. An example of this is a cortisone acetate suspension, consisting of 25 mg/ml or 50 mg/ml cortisone acetate, 4 mg/ml polysorbate 80, 5 mg/ml sodium carboxymethylcellulose and preservatives in isotonic saline (Merck Sharp & Dohme, 1988 PDR, pp. 1297–1299). Indications are for intra-muscular use only, when oral therapy is not feasible. In some cases an organic solvent and detergent are combined. A pre-anesthetic sedative product containing 2 mg/ml or 4 mg/ml lorazepam and 0.18 ml/ml polyethylene glycol 400 (non-ionic detergent) in propylene glycol is available for IM injection or IV injection after dilution. It is reported to cause pain and burning with 17% incidence with IM injection (Wyeth, 1988 PDR, pp. 2258–2259).

FORMS DESCRIBED IN THE PATENT AND SCIENTIFIC LITERATURE

Many of the systems in this category make use of fatty acids, "fats", phospholipids, and non-ionic surfactants. For the reader's convenience the chemical and physical nature of these substances will be described briefly in the remainder of this paragraph. Alkali cation salts of fatty acids are "soaps" which tend to form micelles of $\leq 5$ nm diameter when mixed with water. They are also capable of coating larger hydrophobic structures. Esterification of a fatty acid with glycerol ($CH_2OH-CHOH-CH_2-OH$) produces monoglycerides (e.g. glycerol monooleate) are either oils or solids in the pure state, depending on their fatty acid chain lengths and temperature. Under some circumstances they are capable of forming or participating in membranous structures in the presence of excess water. With esterification of two or three OH positions of the glycerol (diglycerides and triglycerides, respectively) this property is lost. Triglycerides are major constituents of "fat" and vegetable oil. They do not form membranes or participate in membrane structures. Phospholipids are 1,2 diacyl esters of glycerol, with the 3 position esterified with phosphate. They are the major building block of biological membranes, and are very tissue compatible. An important and abundant example is lecithin (phosphatidylcholine), in which the phosphate group is esterified with choline, producing a zwitterionic polar head group. In the presence of excess water, phospholipids form membranes of bimolecular thickness. The polar head groups are oriented to the water; the fatty acyl chains form a palisade structure, with their ends abutting in the center of the membrane. Non-ionic detergents (or surfactants) used in drug formulations are high molecular weight polymers of alternating hydrophobic and hydrophilic segments. An often-used and cited example is polyethylene glycol, which has the structure $H(O-CH_2-CH_2)_nOH$. Non-ionic detergents are capable of coating and solublizing hydrophobic oils and solids in aqueous media. They do not form membranes. They lyse biological membranes and are thus not tissue compatible.

Wretlind et al. (U.S. Pat. No. 4,073,943, 1978) described the use of fat emulsions, of the type used for intravenous feeding, as a carrier for the intra-venous administration of water-insoluble drugs. The described examples typically contained 0.5%–3.75% drug and 20% (w/v) vegetable oil as carrier. The drug/oil ratios (or payload) were typically 0.05, and ranged between 0.013 and 0.375. This essentially limits the fat emulsion to intravascular delivery and limits the total amount of drug which can be administered each day (cf. Criterion E, above). This restriction applies to other patents involving IV fat emulsions (Mizushima et al., U.S. Pat. No. 4,613,505, 1986; List et al., U.S. Pat. No. 4,801,455, 1989). The system is the basis of Diazemuls ®, an IV-injectable product of Pharmacia of Canada, containing 0.5% (w/v) diazepam, 15% (w/v) soybean oil and other constituents.

Haynes (U.S. Pat. No. 4,725,442, 1988) described injectable aqueous suspensions of phospholipid coated microdroplets of water-insoluble drugs. The drugs were themselves oils (e.g. inhalation anesthetics) or were dissolved in a pharmacologically-acceptable oil. The present invention offers improved payload for crystalline, water-insoluble drugs.

Liposomes, vesicles formed from membrane-forming phospholipids such as lecithin, were first described by Bangham, Standish & Watkins (in J. Mol. Biol. 13:238, 1965). That publication proposed the bilayer structure described above. Homogenization of phospholipid in water produces multi-lamellar phospholipid vesicles consisting of concentric bilayer membranes. Sonication produces small unilamellar phospholipid vesicles as described by Haung (in Biochem. 8:344, 1969). Liposomes have the ability to entrap polar and highly-charged molecules in their aqueous interiors. The fact that liposomes are a non-antigenic delivery system (Criterion D) is widely appreciated. There are numerous patents directed to their properties of entrapment and delivery of water-soluble drugs. In a smaller number of patents, liposomes have been shown capable of incorporating oil-soluble drugs, but the payloads are low. As examples Schrank (U.S. Pat. No. 4,411,894, 1983) with payload=0.01-0.033 gm diazepam or flunitrazepan/gm phospholipid, Mezei & Nugent (U.S. Pat. No. 4,485,054, 1984) with payload=0.18-0.20 gm progesterone/gm phospholipid plus cholesterol, Dingle et al. (U.S. Pat. No. 4,427,649, 1984) with payload =0.10-0.125 gm fatty acylated steroid/gm phospholipid, or Abra & Szoka (U.S. Pat. No. 4,766,046, 1988) with payload=0.03-0.07 mole amphotericin/mole phospholipid. With the exception of diazepam and flunitrazepan, all of the above drugs are membrane active agents which are expected to incorporate into membranes. That they can not incorporate at levels above 0.2 gm/gm is indicative of an upper limit of the degree of loading and disruption of the palisade structure of the phospholipids in the bilayer.

Sears and Yesair (U.S. Pat. No. 4,298,594, 1981) described incorporation of adriamycin, imidocarb and estradiol decanoate into "microreservoirs", described therein as a mixture of vesicular and non-vesicular structures, consisting of phospholipid and a much lower concentration of cholesterol esters. Drug concentrations were low 0.002%-0.32%, and the payloads were low (0.00066-0.027 gm drug/gm phospholipid plus cholesterol ester.)

The present invention makes use of phospholipid to suspend water-insoluble drugs, but in a completely different way than described in the above liposome patents. Rather than attempting to dissolve the drug in the lipid bilayer, my invention retains the drug in crystalline form and uses the phospholipid to coat the crystal. The phospholipid vesicle is not an integral part of the lecithin-coated microcrystal.

There are numerous examples of drugs coated with wax or "lipoidal materials". However, the examples are directed at oral administration, and in some cases topical administration. For example tristearin (triglyceride of glycerol and stearic acid) is a common constituent of tablets. It is a "fat" with the physical form of a powder or wax at normal temperature (Merck Index, 10th Edition, Merck & Co., Rahway, N.J., 1983, p. 1293). In some cases the coating is melted on (Augart, U.S. Pat. No. 4,483,847, 1984; Kondo, U.S. Pat. No. 4,102,806, 1978). Various improvements of this technique have been patented: Ohkawara et al., U.S. Pat. No. 4,675,236, 1987), again as oral administration forms. A patent of Ghyczy et al. (U.S. Pat. No. 4,378,354, 1983) describes "pills" of non-steroidal anti-inflammatory drugs containing phospholipids.

Forms involving especially small crystals have been termed microcapsules. The microcapsule (exemplified by Morishita et al., U.S. Pat. No. 3,960,757, 1976) is generally a 30-1,200 u capsule of drug coated usually with a water-insoluble material such as ethyl cellulose (Alam & Eichel, U.S. Pat. No. 4,316,884, 1982), wax or insoluble salt of a fatty acid. The sizes of microcapsules are often described in terms of "mesh", with typical ranges of 50-200 mesh (300 um to 75 um), with some examples at least 10 u up to 5 mm. They are used in tablets or to fill capsules. Wax is generally recognized to be water-repelling, and waxy coatings do not lend themselves to aqueous suspensions. Wax-coated microcapsules are primarily directed towards oral use which does not require stable suspensions in aqueous media, injectability and compatibility with tissue, or small size (Criteria A, B, and F, above).

The patent literature contains numerous examples of preparations directed at topical use containing crystalline drugs mixed with glycerol-lipids such as glyceryl monooleate (Reller, U.S. Pat. No. 4,219,548, 1988). The cosmetic literature also offers numerous examples of creams of high water content (cf. Nieper & Melsungen, U.S. Pat. No. 3,274,063, 1966) to which crystalline drugs can be mixed. These creams can not be considered injectable because they constitute a self-adherent mass which does not dissociate to give particles small enough to pass through blood capillaries (Criterion B). Additionally, the tissue- and blood compatibility of the surfaces presented by these topical preparations has not been demonstrated (Criterion A). A more recent example not meeting these criteria and Criterion F is the U.S. Patent of Mezei (U.S. Pat. No. 4,761,228, 1988). It describes the topical application of minoxidil and econazole nitrate to skin at concentrations of 1.2-3%, in a preparation containing multi-lamellar lecithin vesicles. The preparation contained the drug in crystalline form. Some of the drug crystals were within the vesicles, and the others were not associated with them. Multilamellar vesicle sizes were between 1 um and 15 um; crystal sizes were between 1 um and 20 um. The formulation was prepared by codissolution in organic solvents, followed by evaporation, addition of aqueous media and shaking. No information on immediate- or long-term stability was given.

The microsphere consisting of drug incorporated into 1-200 um diameter spheres of heat-hardened serum albumin, with the precipitated drug incorporated therein, was described by Zolle (U.S. Pat. No. 3,937,668, 1976). In some cases it has been described as an injectable form. Widder and Senyei (U.S. Pat. No. 4,345,588, 1982) described the IV injection of albumin microspheres consisting of drug, serum albumin and $Fe_3O_4$ powder in a ratio of 10:125:36. The albumin is crosslinked by formaledhyde. Particle diameter was 10 um. However, the antigenicity question was not addressed. Mosier (U.S. Pat. No. 4,492,720, 1985) described 50 um-350 um diameter spheres designed for "chemoembolization" via intra-arterial delivery. The microspheres consisted of water-soluble drugs bound in a matrix of hydrogenated lard or vegetable oil and stabilized by detergents. Morris (U.S. Pat. No. 4,331,654, 1982) described a lyophilized preparation of <3 um diameter magnetically-localizable microspheres consisting of a core of magnetite ($Fe_3O_4$) coated with a solidified mixture of fatty acid and non-ionic detergent, and containing lecithin as a minor constituent. He suggested, but did not demonstrate, that drugs could be incorporated at a weight ratio of 0.02-0.15 gm drug/gm fatty acid. Blood and tissue compatibility, resuspendability and stability of suspensions were not discussed.

A classification which fulfills the size criterion for injectability is the nanoparticle. Oppenheim et al. (U.S. Pat. No. 4,107,288, 1978) described particles of 120-660 nm diameter consisting of glutaraldehyde-fixed gelatin. These included phenobarbitone at low payload 0.0067-0.0979 gm drug/gm gelatin (denatured collagen). Antigenicity and blood compatibility were not described. Couvreur et al. (U.S. Pat. No. 4,329,332, 1982) described ≦500 nm diameter particles of alkylcyano-acrylate incorporating drug at low payload 0.0012–0.062, and apparently stabilized by detergent. No information was given on blood or tissue compatibility or stability of the suspension.

BRIEF DESCRIPTION OF THE DRAWINGS

FIG. 1 is a schematic representation of the phospholipid-coated microcrystal. The symbol O== is a phospholipid (O is polar head; == is the pair of fatty acyl chains). Diameter is 0.5 um (range 0.05–10 um).

FIG. 2 presents drawings of a field observed with a fluorescent microscope when the 20% (w/v) oxytetracycline, 20% (w/v) egg lecithin microcrystal preparation, doped with Nile Red, was spread on a slide. White indicates high fluorescent intensity.

FIG. 8 shows the time course of anesthesia in the human skin (pin prick) achieved with lecithin-coated 20% (w/v) tetracaine hydroiodic acid microcrystals 8A, compared with tetracaine-HCl solutions 8B.

DESCRIPTION OF THE INVENTION

Figure 2B:
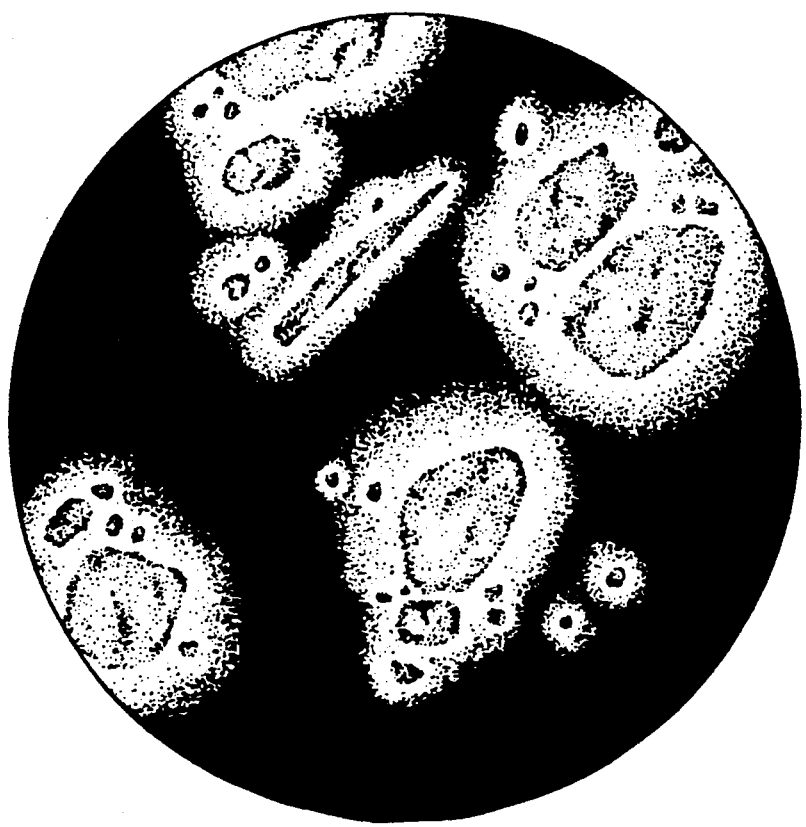
FIG. 2B shows the pattern of oxytetracycline fluorescence. The smaller particles are approx. 0.2 um diameter.

My invention provides a means for creating injectable, tissue-compatible suspensions of water-insoluble drugs at high concentrations. This allows the parenteral (injection) administration of drugs. It is generally applicable to any water-insoluble drug which is in the crystalline state at 37° C. Formulation as a phospholipid-coated microcrystal enables the drug to be injected or otherwise parenterally administered. The formulation is unique in satisfying all of the 6 criteria (tissue-compatibility, $\leq 10$ um size, injectable quantity, non-antigenicity, payload, and physical stability) for a maximally-useful injectable form. The relationship between the microcrystal and the coating phospholipid is depicted schematically in FIG. 1. Central to my invention is the use of the amphipathic or amphiphilic properties of phospholipids in general and lecithin in particular. Webster's Medical Desk Dictionary (Merrian-Webster Inc., Springfield, Mass., 1986) defines amphipathic/amphiphilic as "... consisting of molecules having a polar water-soluble terminal group attached to a water-insoluble hydrocarbon chain." In FIG. 1, the polar head group of the phospholipid is denoted by circles and the hydrophobic hydrocarbon chains are denoted by "sticks". Many substances are amphipathic, including soaps, surfactants and detergents. Unique to my invention is the use of phospholipids to shield the hydrophobic surface of the crystalline drug and to provide additional membranous barriers against reassociation of the crystals. Other amphipathic molecules such as soaps, surfactants and detergents are unable to provide such stable and tissue-compatible structures. Also unique to my invention is the means of forming these stable phospholipid-coated microcrystalline structures. This is described below.

SIZE REDUCTION AND PRIMARY COATING

As described herein, the crystalline drug substance is reduced to <10 um or submicron dimensions in an aqueous medium by sonication or other treatments involving high shear. Lecithin (or other membrane forming lipid), present during the sonication, is itself broken into highly reactive fragments with exposed hydrophobic surfaces. These fragments coat and envelop the submicron crystals creating a primary coating. A requirement for this process is that the lecithin and drug be present together during the sonication or alternative high-energy dispersing process. (Sonication of drug crystals, followed by rapid mixing of pre-formed phospholipid vesicles does not give stable submicron aqueous suspensions of the drug.) The subsection entitled "Methods of Preparation" specifies alternative methods involving inflight evaporative coating and solvent dilution. The common aspect of all of these preparative methods is that the fatty acyl chains of the phospholipid must have direct access to the microcrystal during the coating process.

In my invention, the amphipathic properties of the phospholipid satisfy both the hydrophilic properties of water and the hydrophobic properties of the crystal surface. Also, the phospholipid membrane surface serves as a stationary barrier to reformation of macroscopic crystals. A second useful property of the primary coating is modification of the rate of the dissolution process. Possible structural features of the phospholipid-microcrystal interaction are schematized in FIG. 1.

SECONDARY COATING: PERIPHERAL PHOSPHOLIPID

In addition to making use of lecithin and other membrane-forming lipids as a coating and enveloping material, my invention makes novel use of membrane-forming lipids as mechanical buffers, organizers of aqueous volume and retardants of recrystallization of the drug. This is achieved by excess phospholipid in the form of unilamellar and multi-lamellar phospholipid vesicles which form a secondary coating of the suspended microcrystal. Predominently unilamellar vesicles are formed as a byproduct of the sonication and primary coating process. Their retention in the preparation was found to improve the long-term stability of the formulation. Also, preformed multi-lamellar vesicles (made by homogenization) or uni-lamellar vesicles can be added to the preparation to improve its stability or pharmacokinetics (Example 5). The secondary coating is loosely attached to the coated microcrystal. Peripheral vesicles associate with and dissociate continuously in the preparation. The secondary coating can be removed by repeated centrifugation and resuspension of the preparation (Examples 3 and 11).

Peripheral vesicles forming a secondary coating stabilize the preparation. While not wishing to be bound to any particular theory or mode of action, detailed consideration has suggested the following mechanisms:

They act as volume buffers interposed between the primary-coated microcrystals. The crystalline and microcrystalline drugs are often more dense than the phospholipid which is, in turn, more dense than water. Thus they will tend to settle under the influence of gravity and will experience greater long-range interactions (van der Waals attraction) than the other two constituents. The secondary coating increases the distance of closest approach of the microcrystalline drug cores, thereby decreasing the van der Waals attraction. It is possible that part of the driving force for the secondary coating is van der Waals attraction between the primary-coated microcrystal and the phospholipid vesicle. Phospholipids (notably lecithin) are ideal as the primary and secondary coating because they are strongly hydrated and engage in well-documented short-range repulsive interactions which make them very resistant to aggregation and fusion.

When peripheral phospholipid is present at 20% (w/v), the majority of the aqueous volume of the preparation is enclosed within phospholipid membranes. This serves as a topological barrier to recrystallization of the drug in a preparation during long-term storage. Reformed crystals can not be larger than diameter vesicle or distance between them, both of which can be kept small.

PHYSICAL CHARACTERISTICS OF FORMULATION

Sonication is most conveniently carried out with the drug at concentrations of 5% (w/v) or less and the membrane-forming lipid at 5% or greater. This results in a syringable suspension of coated microcrystals of predominantly sub-micron dimensions, with the particles exhibiting Brownian motion (Examples 2, 3 and 11). Over a period of 1-2 days the microcrystals settle creating a distinct zone in which the drug concentration is 20-40% (w/v). The final concentration and volume are dependent on the choice of the drug and upon the peripheral phospholipid concentration. In most preparations the bottom zone is resuspendable with inversion to give a homogeneous and syringable suspension, even after a period of months. For preparations in which this was not the case, resuspendability was obtained by increasing the peripheral phospholipid concentration.

The slow sedimentation process can be used as a means of concentrating the preparation. Removal of the volume above the sedimentation zone after 1-2 days results in preparations in which the drug is at 20-40% (w/v). Long-term storage results in no further settling. The preparations remain homogeneous, syringable and pharmaceutically acceptable for many months (cf. Examples). Microscopic examination of these preparations reveals separated micron and sub-micron diameter crystals of the drug. The volume between these drug microcrystals is almost completely filled with phospholipid vesicles, visualized by Nile Red staining (cf. Examples 2, 3 and 11). In this concentrated form, the drug microcrystals exhibit only restricted Brownian Motion. Under microscopic observation they are not observed to change position in relation to eachother. They vibrate or "dance in place" about their central position. This partial restriction of motion is probably an important factor in the long-term stability of the preparation.

When stored, concentrated preparations are diluted many thousand-fold into drug-saturated water, the microcrystals retain their micron or sub-micron size.

MODES OF ADMINISTRATION

As noted above, the primary utility of the coated microcrystal is its injectability. Applicable injection sites are any tissue or body cavity. They include but not limited to intra-venous (IV), intra-arterial (IA), intra-muscular (IM), intra-dermal, sub-cutaneous (Sub-Q), intra-articular, cerebro-spinal, epi-dural, intra-costal, intra-peritoneal, intra-tumor, intra-bladder, intra-lesional, sub-conjunctival, etc. In addition, the phospholipid coating and submicron size of the preparation may prove to have advantages for oral use, both as an aqueous suspension and as a lyophilized product. Similarly, the aqueous suspension may show advantages for topical application, instillation into the eye. The preparation can deliver drugs by the inhalation route, in the form of either an aqueous suspension or a lyophilized powder. It is also likely that the preparation will be useful for administration of pesticides and in creating high value biocompatible products, as exemplified by suspension of drugs in drinking water (Example 15).

RATE OF RELEASE

The most important determinant of the rate of release of the drug is the choice of injection site. If the formulation is injected intravenously, it can be released from the microcrystal quite rapidly. If the formulation is injected at high volume into a confined space such as muscle, the net rate of release can be exceedingly slow. The intra-venous case will be considered first.

The blood is a fluid medium which is capable of diluting the preparation 1,000,000-fold within approx. 1 min. When a concentrated lecithin-coated microcrystal preparation is diluted in blood, the individual microcrystals, initially in an environment consisting of other coated microcrystals, peripheral lipid and drug-saturated water, are transferred to an environment consisting of serum proteins, serum lipoproteins and cellular blood elements. My in vitro fractionation experiments (Examples 3 and 11) suggest that the secondary coating will be rapidly lost. All of the blood elements are capable of binding lipophilic molecules and will do so as rapidly as the microcrystal can dissolve. In cases where the drug is sufficiently water soluble, dissolution into the aqueous portion of the blood is sufficient to distribute the drug. When water-solubility is insufficient, a continuous process of dissolution and binding of the drug to blood elements serves to remove the drug from the microcrystals. The rate of dissolution of the microcrystal will depend upon the thickness and stability of its primary coating, the water-solubility of the drug and other physico-chemical parameters. Example 10 shows that the anesthetic alfaxalone can leave the microcrystal and enter the brain within 10 sec of its IV injection. It is possible to reduce the rate of release after IV administration by variation of the thickness of the primary coating or by inclusion of small quantities of water-insoluble oil (such as vitamin E) in the preparation.

With injection into a tissue such as muscle, the preparation does not undergo rapid dilution. It generally remains in the initial elements of volume created by the injection. These are generally macroscopic and there is little flow or agitation. Diffusion the drug out of this volume is slow because of the relatively large distance involved and is further slowed by the low water solubility of the drug. The larger the injected volume and the lower the water solubility, the slower will be the rate of removal of the drug (Example 7). In the extreme, the release process can require upwards of 14 days. For high and fixed volumes and drug concentrations, the rate of removal can be increased by incorporation of hypertonic glucose or carboxycellulose in the vesicles of the secondary coating. This resists the mechanical pressure of the tissue which tends to solidify the injected preparation (Example 5). IM injection is useful to create a depot of drug and to obtain sustained release to the blood over a period of days. Injection directly into the target tissue or lesion is useful because it achieves high and sustained concentrations of the drug at the site where it is needed without involving the rest of the system.

METHODS OF PREPARATION

1. Sonication: The sonication process reduces the size of supra-molecular structures by the process of cavitation. The process creates small empty volumes which collapse, propelling material together at high speed, resulting in shattering and sheer. This simultaneously breaks up the drug crystals and phospholipid lamellae into submicron fragments. The phospholipid membranes are shattered in directions both parallel and perpendicular to their planes, yielding surfaces which can coat the hydrophobic surface of the microcrystal, an which can rejoin to envelope it, respectively. Thus the phospholipid concentration must be adequate for the rate of coating and enveloping to exceed the rate of rejoining of broken crystals. I have observed that sonication usually works well when the drug concentration is 5% (w/v) or lower and when the phospholipid concentration is 5% or greater. The role of the secondary coating of phospholipid vesicles has been described above.

It does not work well if the drug and lipid are sonicated separately and added together. In fact, in the absence of a membrane-forming phospholipid one seldom succeeds in reducing the drug to sub-micron size for even a short time. Sonicated or homogenized lipid can be added to already-prepared coated microcrystals to increase or modify their peripheral lipid content. As described above, the preparation can be concentrated to 20%-40% (w/v) by allowing it to settle.

The product can be put into dry form by lyophilization to yield a powder which can be later reconstituted (Example 6). This is useful when the long-term chemical stability of the to-be-encapsulated drug in an aqueous environment is poor.

2. Methods involving high pressure and shear: The crystalline drug and phospholipid are pre-mixed by high-speed homogenization (as with Waring Blender. Further size reduction and coating can be accomplished by the process of Microfluidization ® (Microfluidics Corp., Newton Mass 02164). The process relies on high shear created by collision of opposing jets of liquid. The apparatus is described by Mayhew et al. in Biochim. Biophys Acta 775: 169-174, 1984. An alternative is high pressure homogenization by means of the French Pressure Cell or "French Press" (SLM Instruments, Urbana, Ill.). In this process, the sample is forced at high pressure and high shear through a narrow orifice and undergoes rapid decompression to atmospheric pressure. Other details are as in #1 above.

3. Sonication or high shear in volatile organic solvents: Microcrystals can be prepared by suspending the crystalline drug and the membrane-forming lipid in a volatile non-polar solvent in which the drug is poorly soluble (dichlorodifluoromethane or dichlorotetrafluroethane or Freon (e.g. trichlorotrifluorethane, c.f. Examples 6 and 8). The suspension is reduced in size by sonication or high-speed shear by the methods described above (#1 or #2). The solvent is removed by evaporation. The resulting powder can be stored for later reconstitution with water or can be reconstituted immediately.

4. Size reduction in air: Drug crystals can also be reduced in size by high speed impact in air. They can be subsequently coated by wetting with a solution of phospholipid or glycerol lipid in a volatile solvent containing lecithin, with the solvent removed by volatilization. The powdered product can be suspended in water. Alternatively, micronized crystals can be wetted by a water-miscible liquid dissolving lecithin and rapidly introduced into an aqueous medium.

5. In-flight crystallization: A solutions of the lipid and drug in a volatile solvent can be sprayed, with the solvent removed by evaporation while in flight. The microcrystals are collected and dried on a smooth surface. The microcrystals can either be stored in the powdered form for later reconstitution with water or can be reconstituted immediately.

6. Solvent dilution: Solutions of lipid and water-insoluble drug are made using a water-miscible organic solvent (e.g. ethanol). The solutions are expressed into an aqueous medium with high agitation or sonication. The solvent dissolves in the water, leaving behind the drug in microcrystalline form coated with the lipid. The organic solvent can be completely removed by filtration or by sedimentation of the coated microcrystals and removal of the supernate.

SELECTION OF THE DRUG TO BE COATED

Any substantially water-insoluble drug which is in the crystalline or solid state at temperatures of 37° C. is applicable. The drug should generally have a water solubility of <5 mg/ml at physiological pH (6.5-7.4). Use of drugs with higher water solubility is not precluded if experimentation shows minimal tendencies to reorganize into macroscopic crystals during the desired shelf life. It is generally desirable to choose a total drug concentration >4× the drug's water solubility, such that at least 80% of the drug is in the microcrystalline form. This choice takes advantage of the high payload and sustained-release characteristics associated with the coated microcrystal. Finally, it is preferred that the drug be intrinsically non-irritating. It is also desirable that the drug be chemically stable in a humid environment. Otherwise it may be necessary to produce lyophilized forms.

The most frequent examples are drugs which are water-insoluble but have moderate-to-good oil solubility. However, oil solubility per se is not a requirement for incorporation into phospholipid-coated microcrystals. Many drugs which have tight crystal structures, high melting points are not particularly water- or oil-soluble. These drugs can also benefit from phospholipid-coated microcrystal formulation. Similarly, it is not necessary for the drug to be uncharged to be put into microcrystalline form. It is only necessary that the water solubility of the crystalline form of the drug be low.

RENDERING A WATER-SOLUBLE DRUG WATER-INSOLUBLE

It is possible to use an intrinsically water-soluble drug in my invention providing that it can be rendered water-insoluble by complexation. For example an insoluble hydroiodic acid (HI) salt of the local anesthetic tetracaine is used to extend its duration of action 5-fold (Example 12). If the drug is charged at physiological pH, it can often be rendered insoluble by substituting a more lipophilic or structured counter-ion. Examples for rendering a positively-charged drug less water soluble include complexation with 2-naphthylenesulfonate (napsylate), gluconate, 1,1' methylene bis (2-hydroxy-3-naphthalene) carboxylic acid (pamoate), tolylsulfonate (tosylate), methanesulfonate (mersylate), glucoheptanoate (gluceptate), bitartrate, polyglutamic acid, succinate, acetate, or behenate (anionic form of waxy fatty acid). In choosing fatty acyl anions it is advisable to select species with either short chain lengths or very long chain lengths, such that the tendency of towards micellarization is minimized. In some cases substitution with bromide, iodide, phosphate or nitrate is sufficient to render the drug less soluble. Examples for rendering a negatively-charged drug less water soluble include complexation with calcium, magnesium or their 1:1 fatty acid salts, and with various amines, including dibenzylethylenediamine (benzathine), N,N' (dihydroabietyl)ethylene diamine (hydrabamine) or polymers such as polylysine. The choice of these counter-ions is made largely on an empirical basis, with stability of the derived crystals and their compatibility with water being primary criteria. Since release of the drug after dilution or injection can involve removal of both the charged and the uncharged forms of both the drug and its counterion, these systems offer both complexity and diversity of kinetics. With sufficient study of the in vitro behavior of the phospholipid-coated microcrystals made from a number of these binary salt systems, and with judicious choice of the most promising examples, the desired in vivo pharmacokinetics can be approximated.

Also, it is possible in some applications, to prepare microcrystals at more extreme pH (4.0–6.4 or 7.5–10.0) in order to suppress ionization and thus decrease the solubility of the drug. The allowable extremes of pH in each particular case will be determined by the concentration of the drug, the number of acid or base equivalents which it carries, its rate of dissolution and the size of the injected compartment and (in terms of shelf life) the stability of the membrane-forming lipid.

SELECTION OF THE MEMBRANE-FORMING LIPIDS FOR COATING

The primary requirement is that the coating lipid be membrane-forming. This is satisfied by all lipids which, in the presence of excess water, make bilayer structures of the type which is well-documented for phospholipid vesicles or liposomes. This requirement is not satisfied by fatty acids, detergents, non-ionic surfactants (e.g. polyethylene glycol) or triglycerides (vegetable oils, tristearin, "fats"). A secondary requirement is that the lipid not have a proclivity for converting into micellar structures. This excludes phospholipids of short chain length (6 or less) or lysolecithin (containing a single fatty acyl chain). High stability of the coating material in membrane form is necessary to keep the drug material from rearranging into macroscopic crystals. This is one reason why non-ionic surfactants do not work well for my intended purpose.

Useful examples of membrane-forming lipids are given below:

CLASS A: Primary phospholipids (usable in pure form) include the following:
  Lecithin (phosphatidyl choline)
  Sphingomyelin
  Synthetic zwitterionic phospholipids or phospholipid analogues To this class belongs all phospholipids which spontaneously form membranes when water is added. These phospholipids can be used in pure form to produce coated-microcrystals. Of all the phospholipids, lecithin is the most useful example because of its high availability and low cost.

CLASS B: Phospholipids capable of calcium-dependent aggregation. These phospholipids include the following:
  Phosphatidic acid
  Phosphatidyl serine
  Phosphatidyl inositol
  Cardiolipin (diphosphatidyl glycerol)
  Phosphatidyl glycerol These lipids carry a negative charge at neutral pH. Preferably these phospholipids can be mixed with lecithin to obtain negatively-charged surfaces which will give repulsion between particles. When introduced into a medium containing 2 mM calcium (such as blood or interstitial), membranes containing these phospholipids are expected to show elevated aggregation and higher reactivity with cell membranes. This can be useful in causing the injected microcrystals to aggregate within the tissue, giving slower release rates. The usefulness of this class is limited by the high cost of these phospholipids, relative to lecithin.

CLASS C: Phosphatidyl ethanolamine promotes aggregation in a calcium-independent manner. It can be used in the pure form to coat microcrystals at pH 9. When the pH is brought to 7, as upon injection into blood or tissue the membranes become reactive, causing the particles to aggregate and to attach to cell membranes. This can have the useful property of slowing the release rate.

CLASS D: Cholesterol and steroids. These can not be used as a sole coating material: They do not form membranes in the pure state. They can be added to the lecithin or other coating material to change its surface activity, the "microviscosity" or distensibility of the coating. With a steroid hormone (estrogen, androgen, mineralo- or glucocorticoid), it is possible to influence the local tissue response to the microcrystals as well as influencing their physical disposition.

CLASS E: Semi-lipoidal molecules can be incorporated into the phospholipid or glycerol lipid membrane and change the surface activity of the microdroplet. Molecules included in this class are the following:

Stearylamine or other long-chained alkyl amines which can be primary, secondary, tertiary or quaternary substituted. These give the microcrystal coating a positive charge and make them more reactive with cell membranes. Benzalkonium chloride is an aromatic example which is particularly useful because it also functions as a preservative against microbiological growth in the preparation.

Fatty acids. These can be incorporated at low concentrations (<0.02 gm/gm phospholipid) to alter the phospholipid packing and reactivity.

CLASS F: Membrane-active agents, glycolipids and glycoproteins to modify surface properties. Examples of membrane-active agents include nystatin, amphotericin B and gramicidin which are surface-active antibiotics. These have been shown to bind to the surfaces of phospholipid membranes and change their permeability. Glycolipids or glycoproteins could be included as a means of modifying surface reactivity. Likewise, antibodies can be coupled to membrane constituents to direct or retain the microcrystal association with targeted cells or tissues. (Glycolipids, glycoproteins, and antibodies are classified as "biologicals". They would have to be screened for pyrogenicity, antigenicity etc. before use, and the process of gaining regulatory approval for such formulations would be more complex.)

CLASS G: Mono-glycerides. These are not phospholipids, but they have been shown capable of forming oriented monolayers and bilayers in the presence of decane (Benz et al. Biochim. Biophys. Acta 394: 323-334, 1975). They may thus prove have some use in coating for microcrystals. Examples of these lipids include, but are not limited to, the following:

1-monopalmitoyl-(rac)-glycerol (Monopalmitin)
1-monocaprylol-(rac)-glycerol (Monocaprylin)
1-monooleoyl-(rac)-glycerol (C18:1, cis-9) (Monoolein)
1-monostearyl-(rac)-glycerol (Monostearin)

COMMERCIALLY AVAILABLE MEMBRANE-FORMING LIPIDS

Several forms of lecithin are contemplated. As an example, egg lecithin (Sigma Chemical Co.) is used in all of the presented examples. It is preferred for its low price and low degree of unsaturation. Lecithin is also available from bovine heart. Soy bean lecithin is less expensive. It has a higher degree of unsaturation. Several synthetic varieties of lecithin are available which differ in chain length from 4 to 19 carbons (Supelco, Inc.). It is believed that lecithins with chain lengths in the biological range (10-18) are useful in various applications. Unsaturated lecithins (dioleoyl, dilinoleoyl; beta oleoyl; alpha-palmito beta oleoyl; alpha palmitoyl beta linoleoyl and alpha oleoyl beta palmitoyl) are also available. Diarachidonyl lecithin (highly unsaturated and a prostaglandin precursor) is also available.

Phosphatidic acid is available from egg or as synthetic compounds (dimyristoyl, dipalmitoyl or distearoyl, Calbiochem). Bovine phosphatidyl serine is available (Supelco or Calbiochem).

Phosphatidyl inositol is available from plant (Supelco) or bovine (Calbiochem) sources. Cardiolipin is available (Supelco) from bovine or bacterial sources. Phosphatidyl glycerol is available from bacterial (Supelco) courses or as synthetic compounds (dimyristoyl or dipalmitoyl; Calbiochem).

Phosphatidyl ethanolamine is available as egg, bacterial, bovine or plasmalogen (Supelco) or as synthetic compounds dioctadecanoyl and dioleoyl analogues and dihexadecyl, dilauryl, dimyristoyl and dipalmitoyl (Supelco and Calbiochem).

Monoglycerides are available from Sigma Chemical Co. (1-monopalmitoyl-(rac)-glycerol, monopalmitin; 1-monocaprylol-(rac)-glycerol, monocaprylin; 1-monoleoyl-(rac)-glycerol (C18:1, cis-9), monoolein; 1-monostearyl-(rac)-glycerol, monostearin).

OTHER CONSTITUENTS

It is possible to add other constituents to the microcrystal to increase its stability or modify its rate of release. For example, pharmacologically-acceptable oils can be added at low weight concentration to facilitate contact between the microcrystal and the phospholipid or glycerol lipid coating. It is necessary that the type of oil and its weight concentration be chosen such that the crystalline drug not be dissolved by the oil and that the coating by the membrane-forming lipid not be disrupted. These relationships can be determined empirically. Useful oils include, but are not limited to, vitamin E, isopropyl myristate, benzyl benzoate, oleyl, alcohol, mineral oil, squalene and vegetable oil. Example 6 gives evidence that incorporation of vitamin E in a lecithin-coated microcrystal preparation of erythromycin decreases the rate of dissolution of the drug, thereby reducing tissue irritation by the drug.

It is also possible to "precoat" the microcrystals by phospholipid-compatible, non-antigenic molecules which are solid at 37° C. Examples include paraffin, tristearin, ethyl oleate, cetostearyl alcohol, cetyl alcohol, myristyl alcohol, stearyl alcohol and petrolatum. For example, these materials can be incorporated into the primary coating by sonication or shear at temperatures above their melting points. Stabilization can be achieved by adding lecithin during the process as temperature is allowed to return to the solidification point of these materials. It is desirable to use low weight concentrations ($\leq 10\%$) such that the payload is not degraded, the rate of dissolution of the drug is not unduly impeded. Also, biodegradability may impose a further limitation. Example 13 describes the lecithin-compatibility of paraffin in micro-particulate form.

SUSPENDING MEDIUM

In the final preparation, the continuous phase is generally water, buffered to a physiologically-acceptable pH and containing an iso-osmotic concentration of sodium chloride or glucose. In certain applications involving intra-muscular injection of large volumes of microcrystals at high concentration, it is useful to increase the osmolarity of the medium (e.g. glucose concentration) to facilitate the spreading of the material in the muscle. As noted above, this can retard the process of compaction after intra-muscular injection. Where permissible, viscosity-increasing agents such as carboxycellulose can be useful to alter the pharmacokinetics following intra-muscular injection and to decrease the rate of sedimentation of the microcrystals upon storage.

In certain applications it is useful to substitute a polar solvent for water, as in Example 7 where albendazole sulfoxide did not show sufficient long-term stability in the presence of water. (Also see Example 5.) Examples of non-aqueous polar solvents which can be used include, but are not limited to the following: glycerin (water-miscible liquid with a dielectric constant of 42.5) and propylene glycol (water-miscible liquid with a dielectric constant of 32). The coated microcrystals can be made in these media, or can be allowed to sediment into these media. The primary requirement is that a substantial portion of the phospholipid or coating material be in membranous form in this solvent. An equally important requirement is that the crystalline material not be sufficiently soluble in the solvent that it will recrystallize.

PRESERVATIVES

Oil-soluble preservatives can be added in process during the primary or coating phase. These include, but are not limited to, benzalkonium chloride, propylparabum, butylparaben, and chlorobutanol. There are also numerous water- and oil-soluble agents which can be added to the finished product as preservatives, including, benzyl alcohol, phenol, sodium benzoate, EDTA, etc.

OPTIONAL LYOPHILIZATION AND RECONSTITUTION

Aqueous microcrystal preparations can be lyophilized to give a dry product which can be reconstituted with water (Example 6). This is particularly useful for a drug which does not have long-term stability in an aqueous environment. It is also possible to conduct the sonication or shear process in a volatile organic solvent in which the crystalline drug is not substantially soluble, and to prepare dry coated microcrystals by solvent evaporation (Example 8). These procedures give microcrystals surrounded by layers of phospholipid in the anhydrous state. Such forms are suitable for oral administration or for reconstitution with water and injection.

DESIGN OF THE FINAL PRODUCT

One skilled in the art following the instructions provided herein will have no difficulty in empirically determining the:

Most convenient method of preparation:

Sonication vs. high pressure and shear vs. methods involving organic solvents vs. impact in air vs. in-flight crystallization vs. solvent dilution Most advantageous form of the drug:

Crystal of neutral drug vs. crystal of charged drug vs. more complex solid forms of the drug Optimal membrane forming lipid:

Based on reactivity and stability of membranes, blood and tissue compatibility and price Optimal conditions for manufacture, including:

Input drug and phospholipid ratio; incorporation of small amounts of oils or waxes as modifying agents; duration of sonication, shear, etc; use of sedimentation as a means of size selection; addition of more peripheral lipid in unilamellar or multi-lamellar form; addition of osmotic or viscosity-affecting agents.

Optimal particle size:

Which can be controlled to a certain extent by the power supplied, the duration of processing, the drug and phospholipid concentrations, And which can be selected between 50 nm and 10 um by sedimentation velocity Optimal compositions to achieve the desired shelf life and pharmacokinetics:

Including study of the effect of the above factors on the pharmacokinetics after injection. Particularly important are the particle size, primary and secondary phospholipid content, and additives to avoid compaction after injection into a tissue.

Most advantageous mode of administration:

Including injection (IV, IA, IM, etc.), oral, topical administration, inhalation, etc.

WEIGHTS AND MEASURES

All parts and percentages reported herein are by weight (w/w) or weight/volume (w/v) percentage, in which the weight or volume in the denominator represents the total weight or volume of the system. Concentrations of water soluble constituents in aqueous solution (e.g. glucose) are given in millimolar concentration (mM = millimoles per liter) referred to the volume of water in the system. All temperatures are reported in degrees Celsius. Diameters or dimensions are given in millimeters (mm = $10^{-3}$ meters), micrometers (um = $10^{-6}$ meters), nanometers (nm = $10^{-9}$ meters) or Angstrom units (=0.1 nm). The compositions of the invention can comprise, consist essentially of or consist of the materials set forth and the process or method can comprise, consist essentially of or consist of the steps set forth with such materials.

DETAILED DESCRIPTION OF THE INVENTION

EXAMPLE 1

Lecithin-coated microcrystals of oxytetracycline (OTC) were prepared by sonication in the following manner:

Into a 150 ml glass beaker, 4.4 gm oxytetracycline dihydrate (Sigma, 0-5750) and 16.0 gm egg lecithin (L-alpha-phosphatidylcholine from egg, Type XV-E, Sigma, P-9671) were added coarsely mixed using a glass stirring rod. Next, an aqueous solution of 300 mM glucose, 10 mM tris adjusted to pH 7.4, was added to give a final volume of 80 ml. The beaker was jacketed with a larger beaker filled with water which was kept in motion by means of a magnetic stirring bar. This, and occasional interruptions of the sonication, allowed for dissipation of heat produced by sonication process. The 1.0 cm diameter probe of a Sonifier ® Cell Disrupter, Model W185D (Heat System and Ultrasonics, Plainview, N.Y.) was immersed in the liquid and mixture was sonicated for a total of 60 min at power stage 10 (nominally 100-150 watts). The temperature of the mixture was not allowed to exceed 60° C. During the sonication, the preparation was titrated with 1.2M HCl to achieve a final pH of 5.0. Sonication resulted in an opaque yellowish-beige suspension. Next, the preparation was covered and allowed to settle for 24 hrs. The bottom 11 ml contained a visible precipitate of OTC at a concentration of 40% (w/v). The supernatant contained phospholipid vesicles. Bottom 22 ml were collected and the precipitate was resuspended with gentle shaking. It contained lecithin-coated microcrystals of OTC. It behaved as a somewhat viscous but syringable liquid.

Fluorimetric analysis and high pressure liquid chromatographic (HPLC) showed that the top phase contained very little oxytetracycline. The bottom phase sampled as the bottom 22 ml contained ≦98% of the added oxytetracycline. It was 20% (w/v) in OTC and 20% (w/v) lecithin. Aliquots were taken from both phases and were diluted into OTC-saturated buffer and were analyzed for diameter (±SD) using a Coulter N4-MD Submicron Particle Analyzer. The top phase was analyzed for particle size was found to have diameters of 30.5±8 nm (77%) and <3,000 nm corresponding to unilamellar and multilamellar phospholipid vesicles, respectively. The top phase was discarded. The lecithin-coated OTC microcrystal fraction had the following weight-averaged particle size distribution: 980±460 (SD) nm, 59%; 2,880±400 (SD) nm, 41%. Analysis of the preparation by electron microscopy using negative staining corroborated the above findings. Several preparations were made as described above and were filled into rubber-stoppered glass ampules and glass bottles.

With storage over a period of weeks some settling was observed, but the preparation could be rendered homogeneous with three inversions. The preparation retained its properties, including size distribution, OTC concentration, chemical integrity and syringability (20 gauge or narrower) for over 9 months.

The importance of the lecithin coating was demonstrated as follows: 4.4 gm OTC and 75.6 ml glucose solution were sonicated for 60 min as described above, but in absence of lecithin. A coarse suspension was obtained with the following characteristics: (a) Immediate sampling and 1,000-fold dilution into OTC-saturated water gave particles visible to the naked eye. Analysis by the Coulter Submicron Particle Analyzer reported that the particles were "out of range" (>3 um). The analysis did not reveal any particles with diameters <3 um. (b) Within 10 minutes after sonication, all of the OTC had settled to the bottom. The bottom phase was not free-flowing and was not syringable. Within 1 hr after settling, it became a solid mass which could not be resuspended with shaking. Similarly, it was impossible to stabilize this preparation by adding pre-formed phospholipid vesicles to the sonicated OTC immediately after cessation of sonication. Thus sonication with lecithin (or other membrane-forming lipid) is shown to be a critical step in the method of preparation.

EXAMPLE 2

Figure 2A:
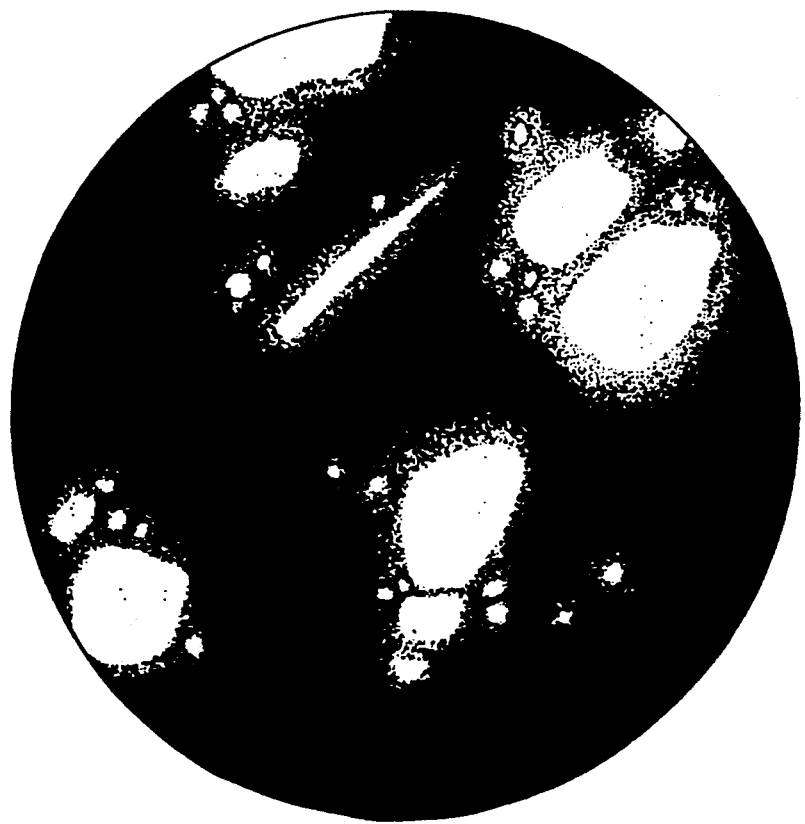
FIG. 2A is of the identical field excited at the Nile Red wavelength. This fluorescence shows the distribution of the lecithin in the preparation.

The preparation of Example 1 was repeated with the following alterations: The preparation was scaled to a total volume of 5.0 ml, the microtip sonicator probe was used and 0.15 mg Nile Red was added at the same time as the lipid. This dye binds to phospholipids and serves as a fluorescent marker for the lecithin. A drop of the 20% (w/v) preparation was spread on a glass slide and observed with a fluorescent microscope (Leitz Wetzlar Dialux 20) at high power. FIG. 2 is a black and white drawing of a typical field. White indicates high fluorescence. With ultra-violet excitation, OTC particles were observed by their intense yellow-green fluorescence. The upper panel of FIG. 2 shows depicts the fluorescent image of OTC. Discrete particles with diameters ranging from approx. 0.2 um and ca. 3 um were observed. The majority of the particles were $\leq 1$ um diameter (number average). The particles had clear boundries, but were surrounded by diffuse yellow-green halo's. The identical field was observed with near ultraviolet excitation to give the Nile Red image associated with the lecithin in the preparation (bottom panel). The Nile Red image shows the lecithin to be surrounding the OTC particles. A halo red fluorescence surrounded the particles, extending 0.3 um to 3 um beyond the boundry of the OTC microcrystal. Empty spaces devoid of both OTC and lecithin, could be readily discerned around all particles situated near the edge of the smear. Occasionally configurations were observed suggesting that two OTC particles were sharing a single phospholipid halo.

Brownian Motion was observed in the sample. The larger (>1 um diameter) particles which settled on the glass slide showed no Brownian Motion, or highly restricted motion. Particles of $\leq 1$ um diameter showed Brownian Motion, moving between the larger particles. Observations in regions of low concentration showed that no particle could move a distance greater than approx. $\frac{1}{4}$ its diameter without its halo experiencing a corresponding movement. Furthermore, direct collisions of the particles were never observed. These observations explain the remarkable stability of the microcrystal suspensions of my invention: The lecithin coats the microcrystal, supplying both a hydrophobic surface for contact with the crystalline surface and a hydrophilic surface for contact with water. The coated surface is enveloped by numerous layers of lecithin in membrane form, as revealed by the Nile Red staining. The stability of the envelopment is shown by the fact that the microcrystal always remains within its lecithin halo, as revealed by their respective fluorescence signals. The outer lecithin layers guarantee that the coated microcrystals do not approach closely enough to fuse.

The dissolution behavior of the lecithin-coated microcrystals was observed under the fluorescent microscope by adding a large quantity of distilled water. The cover slip was raised and a drop of water was balanced next to it, making contact with the smear. The cover slip was floated, and the behavior of the preparation was observed. The smaller particles (approx. 0.2–1.0 um) moved with the water flow. The Nile Red fluorescent halo moved together with the fluorescent OTC particle, and the brightness of the two fluorescent signals initially remained in constant proportion. As the particle moved into the distilled water, the OTC signal dimmed, suggesting that the microcrystal was dissolving. Only a small fraction of the Nile Red image and intensity was lost, suggesting that the lecithin coating was a persisting structure. The dissolution behavior of the larger particles which were generally more firmly attached to the slide was somewhat different. The streaming caused them to shed a large portion of their lipid. The larger microcrystals were then observed to crack, splitting off shards each of which carried away a portion of the Nile Red halo with it.

Dissociation behavior was also studied using the Coulter N4-MD Submicron Particle Sizer. As stated in Example 1, when the preparation is diluted 1,000× into isotonic glucose buffer saturated with OTC, the preparation is stable and particles sizes of 980±460 nm and 2,880±400 nm were observed. When the dilution was made 1,000× into distilled water, rapid alteration of the preparation was observed. Dissolution was expected since the final OTC concentration becomes 0.2 mg/ml, which is lower than the aqueous solubility of the drug (about 1 mg/ml). Dissolution was observed, but it was accompanied by the formation of some particles with diameters greater than 3 um.

EXAMPLE 3

A Nile Red "doped" lecithin-coated microcrystal preparation of oxytetracycline was made and the following fractionation experiment was carried out to delineate the relationship between the primary and secondary phospholipid coatings for the larger-diameter (1.0–1.9 um) coated microcrystals.

Oxytetracycline (2.0 gm), lecithin (8.0 gm) and Nile Red (1.5 mg) were added to 40 ml of isotonic glucose and sonicated for 30 min. The preparation was allowed to concentrate to 20% (w/v) OTC by sedimentation overnight. The volume of this preparation was 10 ml. Small aliquots were taken for fluorimetric assay of Nile Red concentration, phospholipid analysis (by ammonium ferrothiocyanate extraction) and for observation under a fluorescence microscope. Then the preparation was centrifuged with a clinical centrifuge at medium speed for 15 min. This resulted in a visible precipitate of 2.0 ml volume. The top phase was separated, and a aliquots were analyzed (1st supernate). The bottom phase was resuspended to a final volume of 10 ml by addition of isotonic glucose. Aliquots of this were analyzed (1st wash). This was repeated to give a total of 5 washings. The procedure removed the small (0.1–0.3 um) diameter coated microcrystals and loosely attached phospholipid vesicles. This allowed the large (1–3 um diameter) coated microcrystals to be isolated and enabled their phospholipid/drug ratio to be assessed.

with ethanol and the oxytetracycline concentration was determined fluorimetrically.

Figure 3:
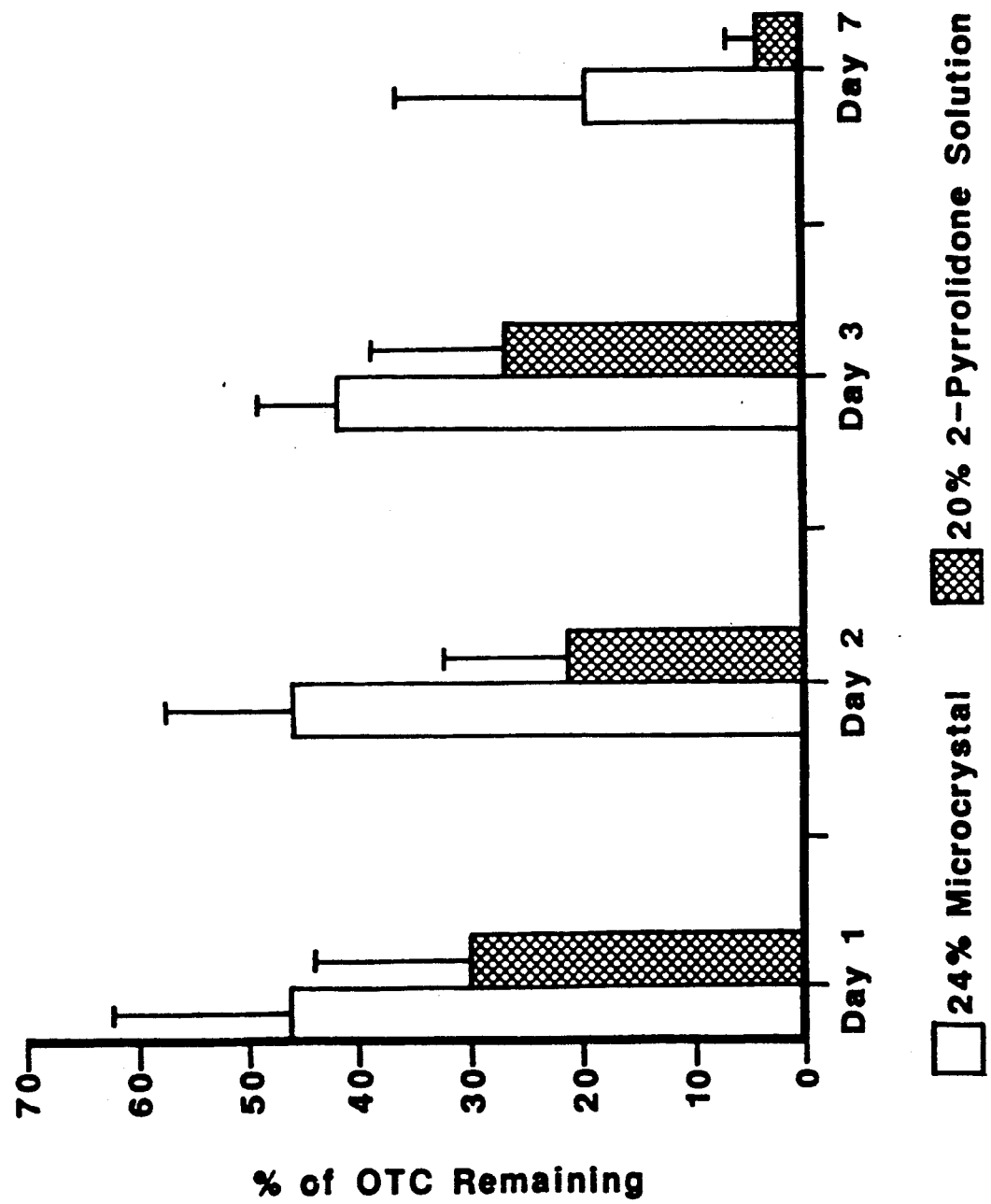
FIG. 3 shows the percent of oxytetracycline remaining in the leg muscle of rats (n=4) after injection of 0.1 ml of 20% OTC in microcrystaline form coated with 5% egg lecithin. The data for days 1–7 post-injection are compared with results for the same quantity of OTC injected as a commercial 2-methyl-pyrolidone solution.

FIG. 3 shows that the oxytetracycline is released slowly from the muscle when injected in the lecithin-coated microcrystal form, with approx. 20% of the injected dose remaining in the muscle after 7 days. The release is substantially slower than the commercial pyr-

TABLE 1

| Step | [OTC] | [Nile Red] | [Lecithin] | Microscopic Observations |
|---|---|---|---|---|
| Prep. | 19.55% | 100 units | 127 ± 7 mg/ml | Observed OTC crystals 0.1–1.5 um diameter. All crystals had bright Nile Red halo with outer diameter ca. 2 × that of crystals. Small crystals and their halos showed Brownian Movement between larger crystals and their halos. The latter were largely stationary. |
| 1st wash | 19.55% | 18.7 units | 20 ± 3 mg/ml | Observed OTC crystals 0.1–1.9 um diameter. Smaller crystals (0.1–0.3 um) were in lesser abundance. A substantial fraction was lost to supernate of first wash. Brownian Movement was as described above. Nile Red halos were reduced to ca. 1.5 × the crystal diameter and were dimmer. |
| 2nd wash | 18.89% | 2.6 units | 247 ± 75 ug/ml | Sizes, composition and movement were similar to those observed in 1st wash, but the Nile Red intensity was much lower. |
| 3rd wash | 18.89% | 0.7 units | 99 ± 10 ug/ml | Sizes, composition and movement were similar to 2nd wash, but the Nile Red intensity was still lower. |
| 4th wash | 18.40% | 0.3 units | 53 ± 53 ug/ml | Sizes, composition and movement were similar to 3rd wash, but Nile Red intensity was very faint on large crystals, and not visible on small crystals. |
| 5th wash | 17.07% | 0.4 units | 160 ± 50 ug/ml | Same as 4th wash, but crystals were grouped in clusters of 5–10. |

The observation show that as the larger crystals are repeatedly washed they lose the greatest fraction of their associated lecithin. The amount of associated lipid stabilizes between at the 3rd–5th wash at 108±80 ug/ml or approx. 0.4% of its input value (Nile Red). The thickness of this coating can be estimated from the volume relationships, approximating the density of the OTC and the lecithin as equal (ca. 1.4 gm/cm$^3$). From the Nile Red data the thickness of the layer 15 Angstrom units. This is close to what is expected from a monolayer of extended lecithin molecules. From the phospholipid analysis the estimate is lower (ca. 3 Angstrom units) but the experimental uncertainty is large and the extraction efficiency for the 3rd to 5th samples may have been considerably less than one. The above procedure may underestimate the thickness of the enveloping layer if the latter were stripped off by the forces of centrifugation. For the small (0.1–0.3 um diameter) microcrystals, the Nile Red halo is observed to be tightly associated with the microcrystal while undergoing Brownian Motion. This suggests that its enveloping layer is quite stable.

EXAMPLE 4

Figure 4:
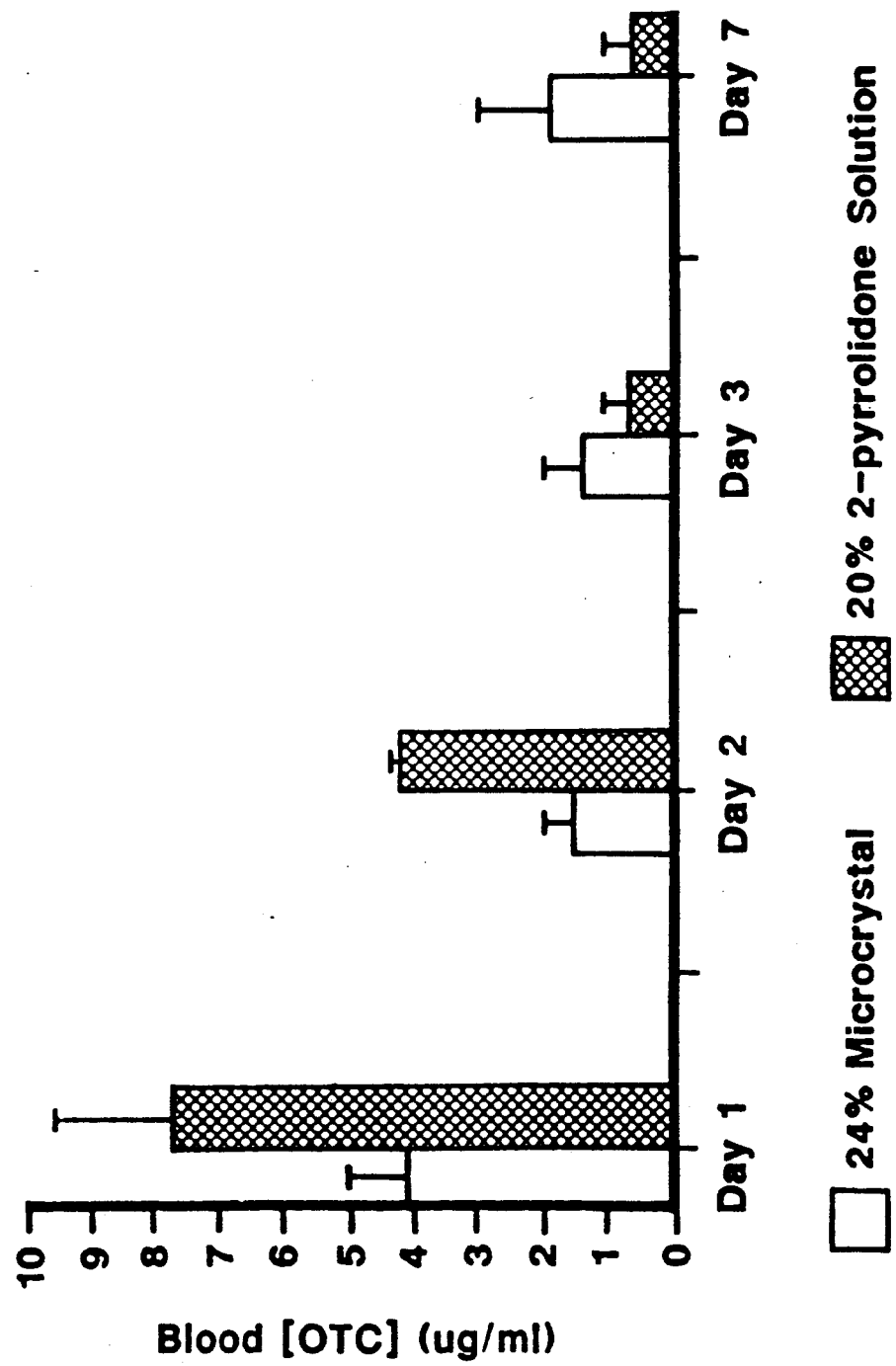
FIG. 4 shows the levels of OTC in central arterial blood in the experiment of FIG. 3.

The pharmacokinetics of lecithin-coated oxytetracycline microcrystals were determined in laboratory rats. The preparation was made essentially as described in Example 1. It contained 24% (w/v) OTC and 20% lecithin. Samples (0.1 ml) were administered by deep intramuscular injections into the hindlegs of laboratory rats. Injections were made (distal to proximal) into the gastrocnemius. Serving as a positive control were 0.1 ml injections of a commercial sample of IM-injectable OTC (Liquamycin® 200, Pfizer), consisting of 200 mg/ml OTC base as amphoteric OTC, 40% (w/v) 2-pyrrolidone, 5.0% povidone (w/v), 1.8% (w/v) magnesium oxide, 0.2% (w/v) sodium formaldehyde sulfoxylate and monoethanolamine and/or HCl as required to adjust the pH. At designated times central arterial blood was taken, the animals were sacrificed and the injected muscles were dissected out and examined grossly and under ultra-violet light for oxytetracycline fluorescence. The blood samples and muscles were extracted rolidone solution. FIG. 4 shows that blood levels from 4 ug/ml to 1.5 ug/ml are sustained over a 7-day period. This can be compared with the commercial solution for which the blood levels drop to 0.5 ug/ml or less within 3 days.

EXAMPLE 5

A large number of preparations of lecithin-coated oxytetracycline microcrystals were formulated at concentrations between 20% (w/v) and 44% (w/v), as described above. The present Example shows how the secondary coating (peripheral vesicles) can be added after the initial sonication step, and how hypertonic glucose and viscosity-increasing agents can be included within its entrapped aqueous volume. Twenty gm of egg lecithin and 5 gm OTC dihydrate were placed in a beaker and an aqueous solution of 12.5% (W/v) glucose, and 10 mM tris buffer, pH 7.4 was added to obtain a final volume of 100 ml. Sonication and pH adjustment were done as in Example 1. Four separate batches were pooled and stored overnight under refrigeration in at screw cap container. After the preparation had settled, the top 87.5% (350 ml) was drawn off leaving lecithin-coated OTC microcrystals and a small portion of the top phase (phospholipid) in suspension. Analysis showed that the lower phase contained 40% (w/v) OTC. (Preparations of OTC could be concentrated to 44% (w/v) by sedimentation.)

Peripheral phospholipid vesicles were prepared separately and admixed with the concentrated lecithin-coated microcrystals. Five gm egg lecithin and 0.1 gm propylparaben (preservative) were added to 45 ml of an aqueous solution of 12.5% glucose and 5% carboxymethylcellulose and the mixture was sonicated at power level 8 for 15 min. This resulted in a thick but syringable suspension of lecithin vesicles entrapping the carboxymethylcellulose and hypertonic glucose.

To complete the formulation, 33 ml of the 40% OTC lecithin-coated microcrystal preparation were mixed with 33 ml of the above peripheral lipid preparation. The mixture was stored in sealed ampules. The final concentrations were 20% (w/v) OTC, 15% (w/v) lecithin, 0.1% (w/v) propylparaben, with the aqueous phase consisting of 12.5% (w/v) glucose and 10 mM tris, pH 5.0.

Experimentation with IM injection in rat showed that preparations made in hypertonic glucose or carboxymethylcellulose, or admixed with peripheral lipid sonicated in the presence of these agents had faster removal of OTC from the injection site than isotonic controls.

Figure 5:
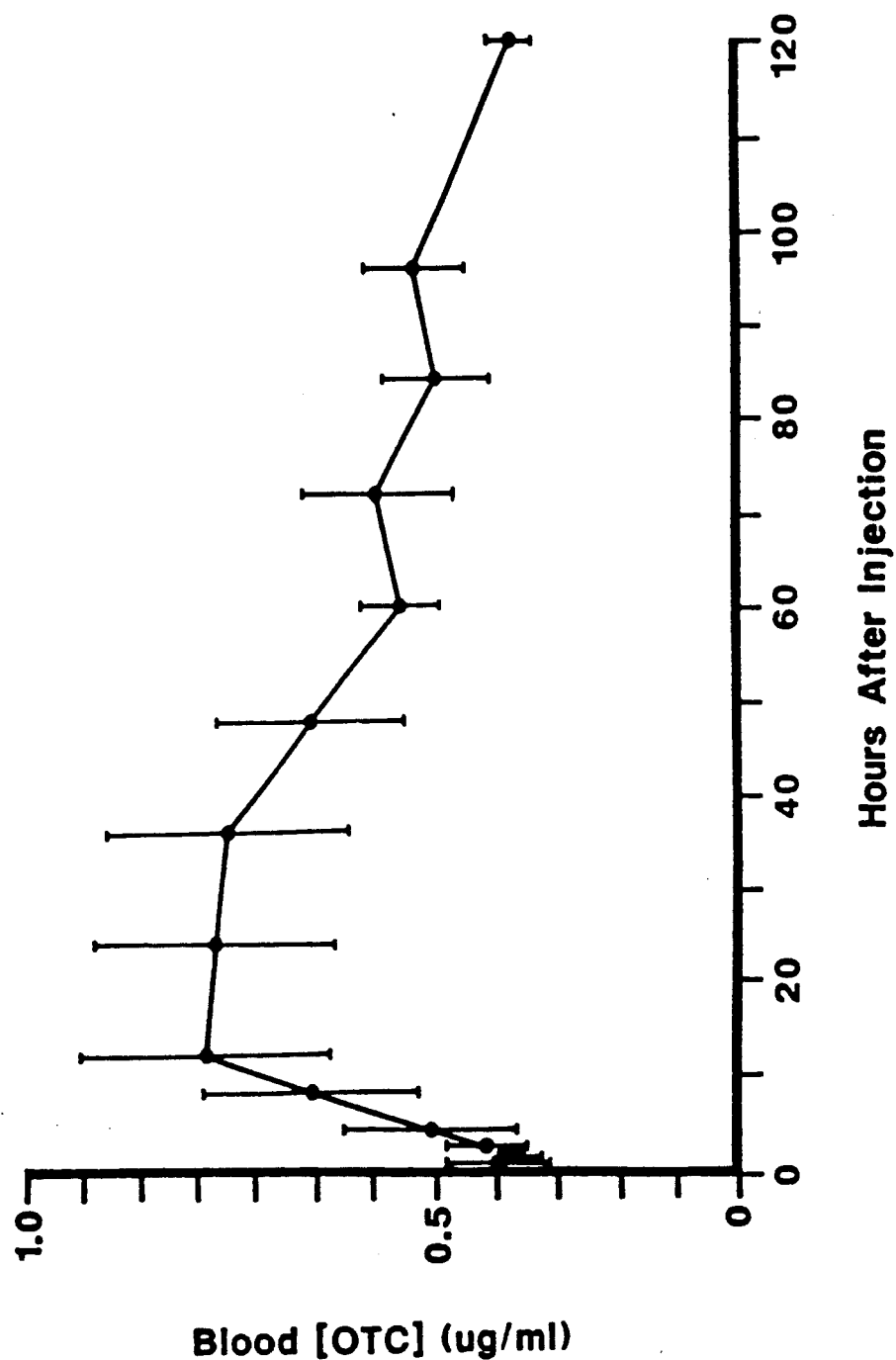
FIG. 5 shows the blood levels of OTC in calf after intra-muscular injection of 20% (w/v) OTC (10% (w/v) lecithin-coated) microcrystals.

The above preparation (denoted Formulation F) was injected intramuscularly into three approx. 300 lb calves at a dose of 9 mg OTC/kg body weight. FIG. 5 shows the average (±SE) blood OTC concentrations as a function of time after injection. The blood concentration vs. time curve is flat, maintaining concentrations between 0.5 ug/ml and 1.0 ug/ml in the time range between 2 and 120 hrs (5 days). Sustained release of this type can be useful, because with suitable high dosing, the animal can receive therapeutic concentrations over a period of 5+ days, without the need for repeated injection.

Results similar to those of FIG. 5 were obtained with the following compositions:

TABLE 2

| [OTC] | [Lecithin] | Treatment of peripheral lecitin | [glucose] | Polar phase |
|---|---|---|---|---|
| 20% | 30% | homogenized | 21% | water |
| 20% | 30% | homogenized | 12% | water |
| 20% | 5% | sonicated | 0% | 45% propylene glycol; 30% water |

All of these samples showed good syringability and physical stability. There were subtle differences in their pharmacokinetics. They gave no pain upon injection or swelling of the injection site. The lack of pain on injection is a particular advantage over commercial solutions.

EXAMPLE 6

Erythromycin, an antibiotic with poor aqueous solubility, was also formulated as lecithin-coated microdroplets in a manner similar to that of Example 4. The aqueous solubility of erythromycin is higher than oxytetracycline at neutral pH (2 mg/ml vs 1.1 mg/ml). Erythromycin is known to be irritating to tissue at high concentration. This was verified by my experimentation, in which a slurry of erythromycin crystals (20% w/v) suspended in propylene glycol was injected intramuscularly (rat). This resulted in extensive pain on injection and damage, such that the rat had to be sacrificed immediately. The following example illustrates how use of lecithin coating reduces the irritation intrinsic to the drug (also see Example 6) and how the irritation can be further reduced by incorporation of a water-insoluble pharmacologically-acceptable oil in the lecithin-coated microcrystal. Table 3 presents results for two compositions prepared by sonication and tested by IM injection in rats.

TABLE 3

| Composition | Characteristics | Obs. with 0.1 ml IM injection |
|---|---|---|
| 20% Erythromycin 15% Lecithin Remainder: 5.4% glucose | 0.7 um particles; syringable; settles in 2 days, resusp. with inversion | Difficulty in walking apparent pain; sacrified at 4 hours; obs. drug deposit and extensive hematoma |
| 20% Erythromycin 15% Lecithin 5% Vitamin E | 0.7 um particles; syringable; settles in 2 days, resusp. | No abnormal behavior or pain on inj.; sacrificed after 4 days; little or no |

TABLE 3-continued

| Composition | Characteristics | Obs. with 0.1 ml IM injection |
|---|---|---|
| Remainder: 5.4% glucose | with inversion hematoma. | drug deposit; small |

The data show that when vitamin E is added, the drug-induced damage is reduced to acceptable levels. The extra protective effect of vitamin E is most likely due to its ability to insert between erythromycin microcrystal and the lecithin coating, creating an additional buffer and barrier towards erythromycin dissolution. This serves as an example in which the lipid coating is modified to reduce the availability of the incorporated drug.

My experimentation with erythromycin formulations has also defined conditions under which lyophilized forms of phospholipid-coated microcrystals are useful. A preparation of 20% erythromycin, 15% lecithin was frozen and placed in a lyophilization apparatus to yield a powder. Upon mixing and swirling with 12% (w/v) glucose it produced a suspension which was syringable and physically stable. Particle sizing gave an average diameter of 0.7 um, identical to the original preparation.

Further experimentation showed that an equivalent lyophilized product can be produced without using water. Sonication was performed in the fluorocarbon Freon TF (trichlorotrifluroethane): Into a sonication vessel, 2 gm erythromycin were mixed with 0.5 gm egg lecithin using a glass stirring rod. Next, 7.5 ml Freon TX was added to the mixture. The mixture was then sonicated at power level 5 for 30 min using the microtip to yield a homogeneous suspension (vessel water jacketed; sonicator cycled on and off). The suspension was placed in a 250 ml Erlemeyer flask and nitrogen gas was blown over the sample. The flask was rotated to distribute the drying material evenly on the bottom. The remaining solid material was dried in a Labconco Bench Top Lyophilizer (Model 75034) overnight. The resulting material was yellowish pellets that resuspended with moderate shaking in a diluent consisting of a presonicated aqueous suspension containing 20% lecithin and 5.4% glucose. The resuspended erythromycin was a syringable, physically stable suspension of 20% (w/v) erythromycin in the form of 0.7 um diameter particles (Coulter N4 Particle Sizer).

Additional experimentation showed that this procedure requires sonication in a solvent such as Freon, in which the solubility of the antibiotic is minimal. The above procedure was repeated, with the sonication taking place in chloroform or ethanol, in which the erythromycin is soluble. In both cases a powder was obtained which did not properly resuspend when added to an aqueous medium. This defines a requirement for the drug to remain almost exclusively in the crystalline state during dispersion and evaporation processes.

EXAMPLE 7

The lecithin-coated microcrystal form has also proven useful for the administration of anthelmintic drugs. For these applications, it is desirable for the drug to be absorbed from the IM injection site into the system within 2 days. A preparation of 10% (w/v) albendazole (8%) lecithin-coated microcrystals was found to give 470 nm diameter particles (Coulter N4 Particle Sizer), to be syringable, to be grossly stable for 60 weeks. Albendazole preparations could be concentrated by sedimentation to 20% (w/v). Upon IM injection of 25 ul into the hind legs of laboratory rats resulted in the following pharmacokinetic behavior:

TABLE 4

| Time, post-inj. | Drug in inj. site | [Drug] in blood |
|---|---|---|
| 4 hr. | 2.0 ± 0.7 mg (80%) | 112.5 ± 11.0 ug/ml |
| 8 hr. | 2.4 ± 0.5 mg (97%) | 62.5 ± 7.8 ug/ml |
| 24 hr. | 1.7 ± 0.5 mg (69%) | <20 ug/ml |

Gross observations of the muscles prior to extraction showed drug deposits with no observable damage to the surrounding tissue.

Injections of 10-20 ml of this preparation intra-muscularly or sub-cutaneously into sheep were well-tolerated. Necropsy at 7 days revealed deposits representing a major fraction of the drug, with little irritation of the surrounding tissue. The slow absorption of the drug into the circulation was probably the result of large volume injected and the low aqueous solubility of albendazole (<0.1 mg/ml). This limited the therapeutic usefulness of the lecithin-coated microcrystal injection form for albendazole, but portends usefulness for other drugs of low water solubility for which slow release over periods of weeks is desired.

The above experimentation was repeated with albendazole sulfoxide, a more water-soluble analogue of the drug. Faster rates of absorption into the blood were obtained. Solubility data for albendazole sulfoxide are: 0.42 mg/ml in water, 17.7 mg/ml in propylene glycol and 179.0 mg/ml in ethanol. Preparations were made with the following compositions: (A) 20% albendazole sulfoxide, 20% egg lecithin, in 5.4% buffered aqueous isotonic glucose; (B) 20% albendazole sulfoxide, 5% lecithin, in propylene glycol. Both preparations normally settled to albendazole sulfoxide concentrations of 20% (w/v). Samples (0.1 ml) of both preparations were injected IM in rats (n=6) and the muscles were examined at necropsy, 2 days post-injection. Both preparations showed small deposits of drug and no irritation of the surrounding tissue. Propylene glycol, which has two OH groups and a dielectric constant of 32, is an example of a polar organic compound which can be substituted for water. In present case, this proved advantageous to the long-term chemical stability of the drug and hence the shelf-life of the preparation.

Experiments with calves showed that a microcrystal preparation of 15% (w/v) albendazole sulfoxide, 3.75% (w/v) lecithin in propylene glycol was particularly useful. Intramuscular injection of ca. 6 ml of this preparation into calf (dose=6 mg/kg) resulted in no pain, and barely noticable swelling at 24 hrs. No drug residue and only slight muscle discoloration were observed upon necropsy after 7 days. Similar results were obtained with 15% (w/v) microcrystalline albendazole sulfoxide plus 5% egg lecithin suspended in a 70/30 mixture of propylene glycol and water. Both of these preparations satisfy current criteria for the usefulness of the preparation in veterinary medicine. Control studies of these preparation without added lecithin showed the drug to be intrinsically irritating, as verified by the animal's behavior, gross observations and histology. This shows that the lecithin-coating helps to reduce the local reaction to this drug.

EXAMPLE 8

Nitroscanate is a water-insoluble anthelmintic compound. An IV- or IM injectable form would be desirable. The compound is not chemically stable in water or in the presence of high relative humidity. It is also chemically reactive with amines. Lecithin-coated microcrystals were made by sonication in Freon as described in Example 6 and were stored in powder form. Reconstitution with aqueous vehicle yields an injectable product. Reconstitution of this product with 5.7 volumes of 20% (w/v) sonicated lecithin containing 0.1% propylparaben in 12.5% glucose yielded a 10% (w/v) suspension of nitroscanate microcrystals. The suspension was syringable and stable for several hours. The particle size was approx. 500 nm, as estimated by microscopic evaluation.

EXAMPLE 9

This example shows how the phospholipid-coated microcrystal can be used as a delivery system for non-steroidal anti-inflammatory drugs in the control of inflammation. The preparation can be injected to create an intra-muscular depot, or can be injected into the tissue to be protected. Indomethacin was taken as an example. The molecule is a carboxylic acid with a pKa of 4.5, but its aqueous solubility at pH 7.0 is only 0.376 mg/ml. To produce a 3% (w/v) solution it is necessary to raise the pH to 9.6. Although its water solubility is poor, the molecule, in the diluted state, shows only moderate oil/water partition coefficients: 55/1, olive oil/water; 85/1, pentanol/water.

A lecithin-coated indomethacin microcrystal preparation was made by the following procedure: Indomethacin (500 mg) was mixed with egg lecithin (2.0 gm) with a glass stirring rod, and an aqueous solution of 300 mM glucose, 10 mM tris (pH 7.4) was added to a final volume of 10 ml. The mixture was sonicated for a total of 30 min at power level 6 using the microtip, with water jacketing and cycling as described previously. This resulted in a homogeneous suspension of coated microcrystals. The preparation was allowed to concentrate by sedimentation to give a final composition of 20% (w/v) indomethacin and 20% (w/v) lecithin. (The highest concentration achievable was 25% (w/v) indomethacin.) An average particle size (Coulter N-4 Particle Sizer) of 100 nm was determined. Long-term stability was good. There was further settling but the preparation could be resuspended with three inversions.

Figure 6:
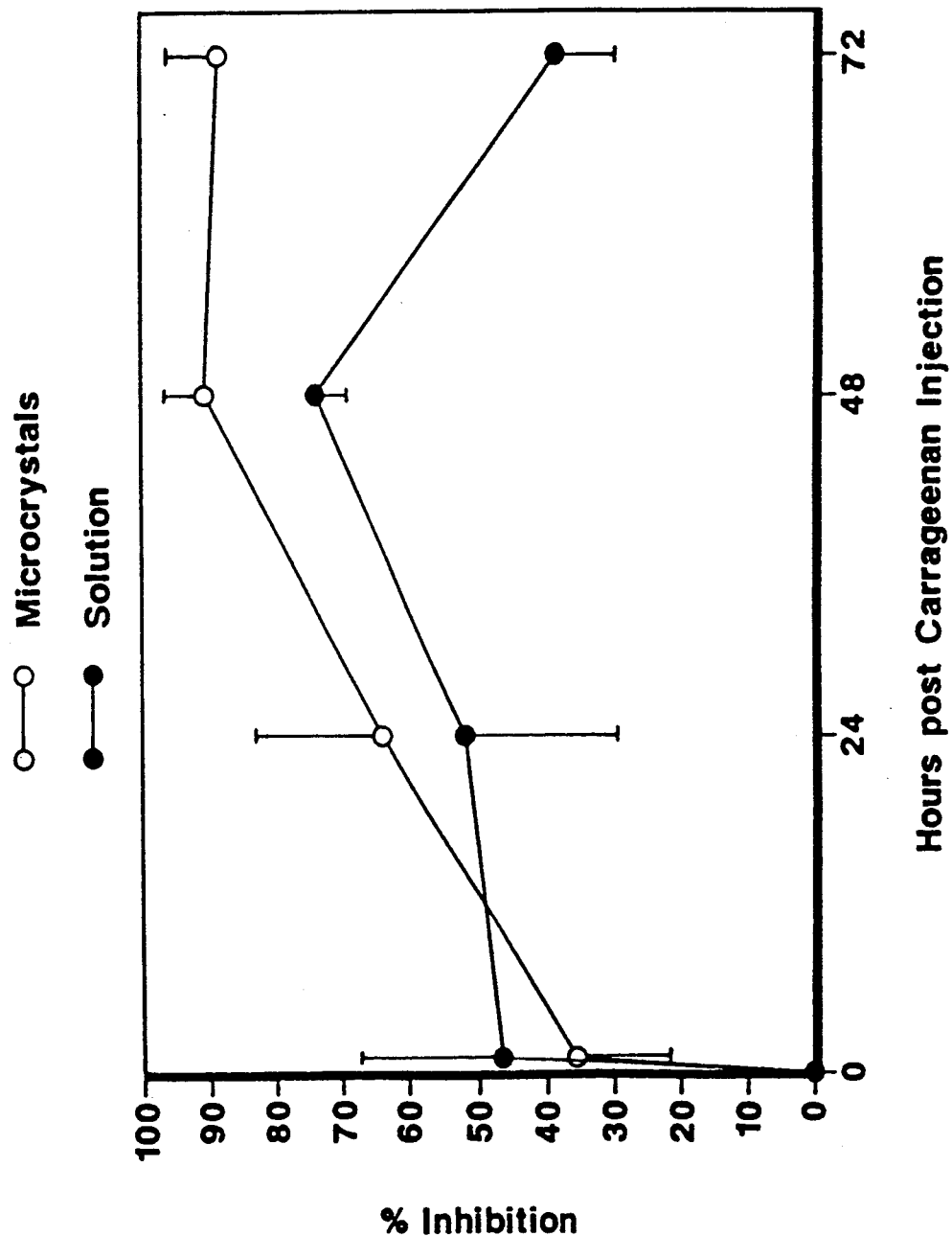
FIG. 6 shows the time course of protection against edema by 5 mg indomethacin injected intra-muscularly as lecithin-coated microcrystals, compared with an equal dose injected as an alkaline solution.

The above preparation was tested in rat as an intra-muscular depot for anti-inflammatory activity using the Carrageenan-induced paw edema model. The dose of was 5 mg indomethacin given by IM injection into the rear leg of 0.025 ml to the preparation or 0.0325 ml of a 15.4% solution at pH 10.5. Efficacy of inhibition of the paw edema was evaluated after Carrageenan challenges at 1, 24, 48 and 72 hr, post-injection. There were 3 rats per time and treatment group. The animals were sacrificed after testing and gross observation of the muscles were made at necropsy. Injections of the microcrystal preparation were not painful as evidenced by lack of appreciable vocalization or retraction of leg during injection and by normal use of the injected leg in the 3-hr period after injection (12 of 12 animals). In contrast, injection of the alkaline solution resulted in vocalization, retraction and limping on the injected leg (12 of 12 animals). FIG. 6 shows the time course of the average percent (±SD) protection against paw edema (opposite leg) after Carrageenan challenge at 72 hr for the two forms. The figure shows that the microcrystal preparation gives 89% while the alkaline solution gives only 38% protection. The rats challenged at 72 hrs were sacrificed and the injected muscles were examined at necropsy. The indomethacin microcrystal-injected muscles appeared normal (3 of 3 animals). In contrast, two of the three muscles injected with the alkaline solution showed damaged areas of ca. 3×6×1 mm dimension, with marked discoloration.

The above demonstrates the ability of the microcrystal formulation to introduce high concentrations of drug into the tissue with minimal irritation. This indicates utility as a vehicle for anti-inflammatory drugs, both in IM depot injections and in injection into the inflammed tissue or space (e.g. synovial fluid).

EXAMPLE 10

This example shows that phospholipid-coated microcrystals are capable of rapidly releasing their contents when injected intravenously. The water-insoluble steroid anesthetic alfaxalone is delivered by this mechanism, becoming available to the brain within 10 sec of its intra-venous injection.

A lecithin-coated alfaxalone microcrystal preparation was made by cosonication of the two constitutents in an aqueous solution 300 mM glucose, 10 mM tris buffer, pH 7.4 to give a preparation with 2% (w/v) alfaxalone, 2% (w/v) egg lecithin. The microcrystals were 548±75 nm diameter (Coulter N4 Sub-Micron Particle Sizer). The preparation was stable for upwards of 4 months. It separated to give a free-flowing sediment which mixed with inversion, and was completely resuspended with shaking.

The following data show that the preparation gives rapid general anesthesia with intra-venous injection: The above preparation (0.11–0.25 ml) was injected intravenously (tail vein) into 200–250 gm female rats (Harlen S-D) to give a doses of 10, 15 or 20 mg/kg. A dose of 10 mg/Kg rendered 6 of 10 rats unconscious. This dose thus approximates the $EC_{50}$. Doses of 15 mg/Kg and 20 mg/Kg rendered all of the animals unconscious (3/3 and 10/10, respectively). The animals were rendered unconscious within 10 sec of commencement of injection. Anesthesia was as fast as the injection which itself required 15 sec. Four types of qualitative and quantitative data were recorded as a function of dosing level: (a) Characteristic spontaneous behavioral changes with emergence from anesthesia, (b) threshold for vocalization with electrical stimulation and (c) surgical anesthesia tested by abdominal incision.

(a) The first indication that the process of emergence had begun was the onset of periodic spasms. For dosing at 20 mg/Kg these occurred at 30.6±16.8 min (±SD, n±10). This was followed by arousal and struggling to right which occurred at 50.6±22.0 min. righting at 57.9±22.4 min. The animals regained normal responses and spontaneous behavior at 84.0±25.5 min.

Figure 7:
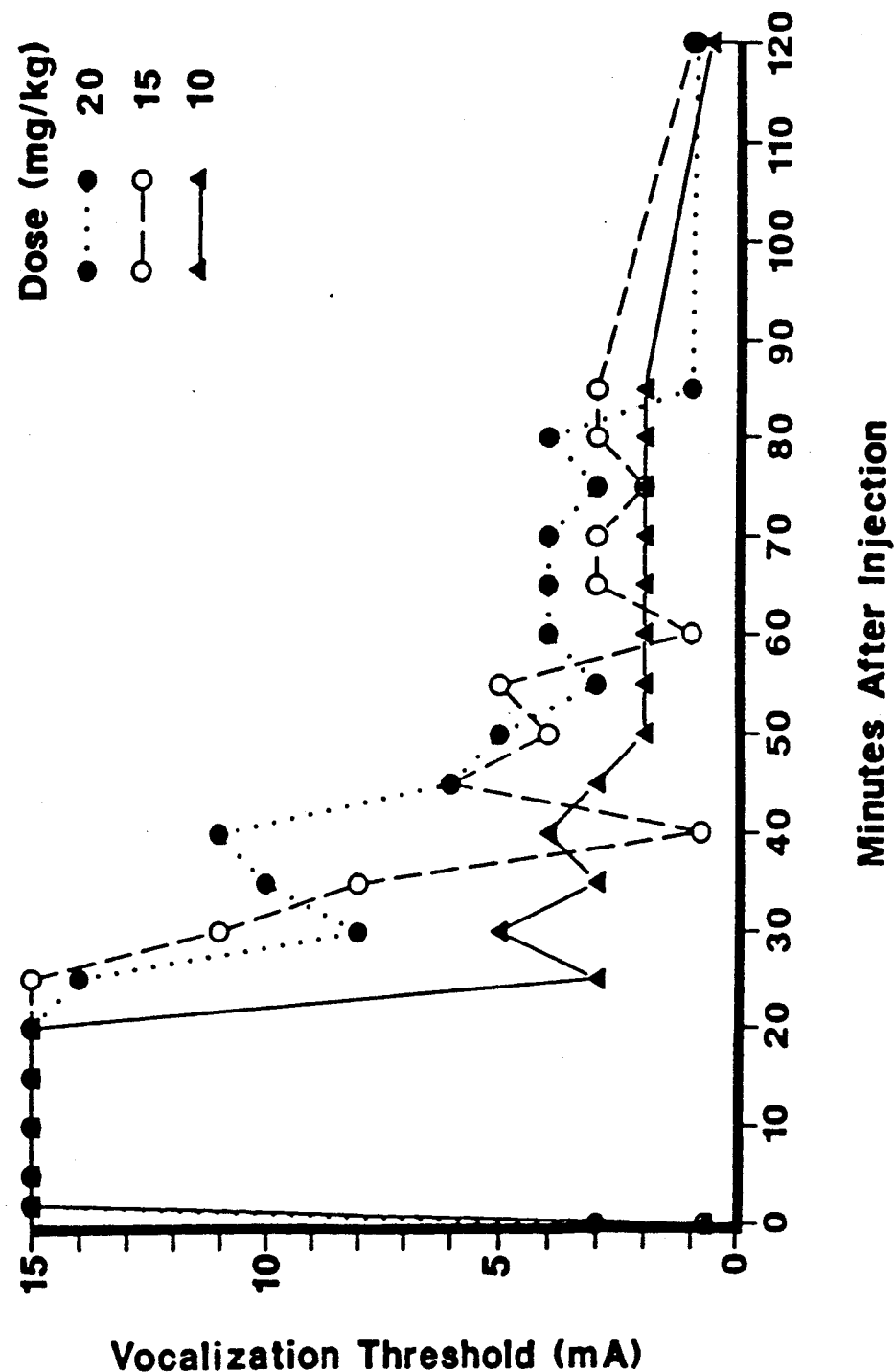
FIG. 7 shows typical time courses of the level anesthesia in rats measured as vocalization threshold (mAmp) to intradermal electrical stimuli after intravenous injection of lecithin-coated alphaxalone microcrystals.

(b) The threshold for vocalization to electrical stimulation via intra-dermal electrodes was tested (needle electrodes in the skin of the back, 3 mm apart; Grass S44 Stimulator and Stimulus Isolation Unit; square waves of 1.5 msec width at 50 Hz; duration of stimulus=2 sec; amplitude measured in mAmp). Vocalization thresholds>7.0 mAmp represent very high anesthesia; thresholds in the >2.0 mAmp range represent intermediate level anesthesia. In unanesthetized human skin (intradermal insertion in leg) a 7 mAmp stimulus causes intolerable pain and a 2.0 mAmp stimulus causes sharp pain. At all three doses, all rats which were rendered unconscious showed immeasurably high thresholds for vocalization: No vocalization was obtained for a maximal 15 mAmp stimulus. FIG. 7 shows typical results for individual rats. The following summarizes the observations with the three dosage groups (3 rats per group): Immeasurably high anesthesia lasted for at least 5 min for all the animals rendered unconscious at the 10 and 15 mg/Kg doses, and for at least 15 min for all animals at the 20 mg/Kg dose. The duration of high level anesthesia increased as a function of dose with times of 26.7±20.8 min for 10 mg/Kg, 35.0±20.0 min for 15 mg/Kg, and 41.7±7.6 min for 20 mg/Kg. The corresponding times for intermediate level anesthesia were 35±15.0 min, 66.7±12.6 min and 63.3±15.3 min. Thresholds of all treated rats returned to baseline levels within two hours of injection.

(c) Surgical anesthesia was tested in a separate group of rats at times approaching the longest time at which the electrical threshold was >15 mAmp. At 10 mg/Kg dose, none of three animals tested responded to incisions opening the abdominal cavity at t=15 min post-injection. At 20 mg/Kg, none of the three animals tested responded to opening the abdominal cavity at t=45 min post-injection. (Immediately after this demonstration of surgical anesthesia, the animals were sacrificed by $CO_2$ asphixiation.)

The above data show that lecithin-coated alfaxalone microcrystals can dissolve and enter the brain and produce general anesthesia within 10 sec of their intra-venous injection. The data also show that the preparation has utility as an induction agent and as an injectable general anesthetic.

EXAMPLE 11

In this example, the alfaxalone preparation of Example 10 is characterized with respect to structure and dissolution behavior. A 2% (w/v) alfaxalone preparation was made by sonicating the drug at 2% (w/v) together with 2% (w/v) egg lecithin and 0.05% Nile Red in a medium of 300 mM glucose, 10 mM tris (pH 7.4) at high power for 20 min. As in Example 3, Nile Red, a fluorescent dye which has affinity for lipids and phospholipids, was used to visualize and track the lecithin in the preparation. Analysis with the Coulter N4 Sub-Micron Particle Analyzer immediately after dilution into an alfaxalone-saturated solution gave an average particle diameter of 0.52±0.03 um. Visualization of the preparation on a slide using a Leitz Wetzlar Dialux 20 Fluorescent Microscope revealed particles of this size. The particles consisted of colorless birefringent crystals of spherical or rounded shape surrounded by an intense halo of red fluorescence with a diameter of approx. 1.2 to 1.7 times that of the crystal. The fluorescence was intense near the crystal surface and was progressively more diffuse as a function of distance from the crystal surface.

The proportion of primary vs secondary lecithin coating was determined in a fractionation experiment of the type described in Example 3. The preparation was sedimented in a clinical (blood) centrifuge at medium speed for 15 min. The supernate was drawn off. Aliquots (10 ul) of the original preparation and its supernate were added to a cuvette containing 2.5 ml ethanol and Nile Red fluorescence (Fl) was measured in a fluorometer. The precipitate was resuspended in the glucose/tris medium to reconstitute the original volume, small portions were removed for analysis with the particle sizer and microscopic observation. This sequence was repeated for a total of three times. Table 5 shows the behavior of the particle size.

TABLE 5

Behavior of Alfaxalone Preparation with Repeated Centrifugation and Resuspension

| Preparation | Nile Red Fluorescence (Fl) | | Particle Diameter |
|---|---|---|---|
| | Fl. Total | Fl. Supernate | |
| Original | 292.0 | 310.0 | 0.52 ± 0.03 um |
| 1st Resusp. | 24.0 | 13.5 | 2.4 ± 0.7 um |
| 2nd Resusp. | 9.5 | 5.0 | >3.0 um |
| 3rd Resusp. | 6.5 | 6.5 | >3.0 um |

Microscopic observation of the 1st resuspension showed that the microcrystals retained their Nile Red halos, but that the halos were much thinner and less intense. Also, the microcrystals were clumped in aggregates of ca. 2.5 um diameter. Thin layers of Nile Red were visible between the microcrystals in the aggregate. Observation of the 2nd and 3rd resuspensions revealed still larger aggregates (of diameter approx. 8× that of particles of the original preparation). The aggregates showed a faint pink fluorescence.

The fluorescence data in Table 5 show that 98% of the lecithin in the preparation was peripheral phospholipid (FIG. 1) which could be dissociated by washing. The 2.22% of the lecithin, as reported by Nile Red fluorescence, is tightly associated with the alfaxalone microcrystals. This represents the primary coating. Assuming equal densities of the drug and lecithin, one can readily calculate that distribution of this amount of lecithin on a 520 nm diameter microcrystal would result in a layer 1.9 nm or 19 Angstroms thick. This is very close to the expected thickness of a monolayer of lecithin. The experiment also demonstrates the role of the peripheral lecithin in preventing aggregation of the microcrystals. Its removal allows the microcrystals to come into closer proximity and to be aggregated by the action of long-range forces.

EXAMPLE 12

The following example shows how the phospholipid-coated microcrystal can be used as a means of producing long-duration anesthesia of the skin with a single injection. Cherney (U.S. Pat. No. 2,803,582, 1957) described how the water-soluble local anesthetic tetracaine can be rendered water insoluble by formation of the hydroiodic acid (HI) salt. Goodman and Gillman's "The Pharmacological Basis of Therapeutics (7th Ed., MacMillan Publishing Co., New York, 1985, p. 312) cite a study (Cherney, L. S. Anesth. Analg. 42:477–481, 1963) showing that crystals of this salt can be sprinkled into surgical wounds to provide local anesthesia of 45 hr. duration. However, reference to the 1988 PDR indicates that hydroiodic acid salt of tetracaine is not commercially available for clinical use in the U.S. The present example shows how the utility of Cherney's invention can be increased by making it lecithin-coated microcrystals.

Insoluble tetracaine-H-I was prepared by adding potassium iodide (KI) to a saturated aqueous solution of tetracaine-H-Cl. The precipitate was resuspended and washed several times with water and then dried. For preparation A, 10 gm of tetracaine-H-I and 1 gm egg lecithin were added to a test tube, and 5.4% glucose, 10 mM tris, pH 7.0 was added to a final volume of 10 ml. The material was sonicated (with temperature control) for a total of 20 min to yield a white suspension. This was allowed to settle overnight, and the top half was discarded. Preparation B was made in a similar manner. Tetracaine-H-I (0.50 gm) and egg lecithin (1.0 gm) were consonicated in 10 ml volume. The top 7.5 ml were discarded and the bottom 2.5 ml were resuspended to give the final preparation. Both preparations were 20% (w/v) tetracaine-H-I and 10% (w/v) egg lecithin. Both preparations showed the tendency to sediment to give 30% (w/v) tetracaine-H-I. The long-term stability of both preparations was good.

Preparation A (0.1 ml) was injected intradermally in the skin of the backs of rats raising a ca. 1.0 cm diameter wheal which was demarcated with a felt tip pen. The degree of anesthesia in the injected skin was determined by the shock vocalization test using indwelling intradermal electrodes positioned in the center of the injected area. The threshold for vocalization was immeasurable high (>15 mAmp) during the first three hours after injection. Four rats were tested during the time-interval 22-25 hr. post-injection. This group had an average (±SD) vocalization threshold of 6.6±2.6 mAmp, indicating good anesthesia. Retesting of this group at 41-44 hr. showed that the anesthesia had subsided. For three of the four animals the skin appeared normal. One animal showed an approx. 2 mm diameter brownish spot in the middle of the injected skin. As a control, two animals were injected with 0.1 ml of tetracaine hydrochloride solution. This resulted in high levels of anesthesia (>15 mAmp) in the initial, but the anesthetic solution caused severe damage to the tissue with scabbing observed on the second day such that measurement of anesthesia was neither practical nor meaningful. This was verified by the results in two additional rats with two injections each. All four injected areas were completely brown and scabbed at 24 hrs and craters were observed at 48 hrs.

The Inventor carried out self-experimentation with Preparation B. I made two intradermal injections of 0.15 ml of Preparation B into the skin of my calf, right leg, inside, at sites 12 cm and 22 cm below the knee. The injections raised weals approx. 1.1 cm in diameter. There was no pain on injection. The weals subsided within ca. 30 sec. The injected sites were tested for pin prick and cold stimulus anesthesia for the next 24 hr. FIG. 8 shows pin prick anesthesia on a 5-point scale (4/4=full insensitivity, 0/4=full sensitivity, to the sharpness of the pin). The figure also shows observations with 2% and 5% tetracaine-H-Cl solutions. The lecithin-coated microcrystal preparation showed complete anesthesia for 7-9 hrs after the injection, with return to 50% sensitivity at 12½-14½ hrs, and complete reversal at 16-21 hrs. The injection did not produce irritation. At 11 min or 1½ hr, a slight erythrema was observed. The injected areas appeared and felt completely normal at 24 hrs. The only reliable means of differentiation of injected and uninjected tissue was a greater sensitivity to vigorous rubbing 1-5 days post-injection.

As a control for the above, I injected myself with 0.15 ml volumes of solutions of 1%, 2% and 5% tetracaine-H-Cl. In attempt to make the concentrated solutions less damaging, the pH was adjusted from 5.3 to 6.5. Physiological tonicity was maintained by including glucose (4.3%, 3.2% and 0%, respectively). FIG. 8 shows that these solutions produced full anesthesia of not more than 2 hr. duration. The 1% and 2% tetracaine-H-Cl solutions produced only mild erthrema, with return to normal color when the anesthesia subsided. The 5% tetracaine-H-Cl solution produced a bright red spot (7 mm diameter) in the center and hardness at 27 min. The presented anesthesia values were taken at its periphery. The site was sore after anesthesia had subsided. The red spot resolved into a scab at 7 days which persisted to 21 days. At 48 days (the time of this writing) the site has a 2 mm diameter scab surrounded by a 1 cm diameter circle of pinkish skin, sensitive to the touch and raised approx. 1 mm. This poor outcome with the 5% (w/v) tetracaine solution is in stark contrast to the excellent results obtained with the 20% (w/v) tetracaine-H-I microcrystal.

The above data show that the use of the lecithin-coated microcrystal method in conjunction with the invention of Cherney allows the anesthetic to be injected at over 4 times higher concentration, producing safe, reversible anesthesia of 5 times longer duration.

EXAMPLE 13

This example shows that particles of waxy substances can be coated and stabilized with a layer of lecithin. These phospholipid-coated microparticles can be made from phospholipid-compatible solid materials which melt between physiological temperature (37° C.) and 100° C. The present example illustrates this using paraffin wax. Paraffin (3.35 gm) was melted in a water bath at 60° C. Egg lecithin (1.35 gm egg lecithin) was put in a beaker and an aqueous solution of 300 mM glucose, 10 mM tris (pH 7.0) was added a final volume of 47 ml and homogenized. The liquid paraffin was added to the homogenized lecithin and the mixture was sonicated for 30 min to obtain a milky uniform suspension. The beaker was covered and allowed to cool to room temperature. The result was a suspension of lecithin-coated submicron diameter paraffin particles which was stable in excess of two weeks. Repetition of the above in the absence of phospholipid resulted in precipitation of solid paraffin.

The above example shows that it is possible to make lecithin-coated microparticles from a material with a melting point below the boiling point of water and above that of the intended temperature of use (37° C.). Pharmaceutically acceptable waxes and solids, of biological and synthetic origin, include but not limited to hydrogenated castor oil, cetostearyl alcohol, cetyl alcohol, cetyl esters wax, myristyl alcohol, petrolatum, paraffin, and various waxes (emulsifying, microcrystalline, white, yellow, etc.). It is also possible to use these materials to provide a waxy coating for the drug microcrystals, which is in turn coated with phospholipid. The waxy coating will further slow the rate of release of the drug, thus prolonging its duration of action.

Lecithin-coated microparticles of paraffin, or alternatively tristearin as a biodegradable wax, will have very long lifetimes in injected tissues. It is likely that they will be useful for the fixation and entrapment (cf. Example 16) of water-soluble antigens or membrane fragments in muscle or skin to increase the efficiency of vaccination (use as adjuvant).

EXAMPLE 14

The following example shows that lecithin-coated microcrystals can be formed in the presence of a water-immiscible organic solvent in which the crystalline drug is not soluble. The example is based on the muscle relaxant dantrolene. Its physical form is bright orange crystals with a melting point of 279°-280° C. and with low water solubility. Dantrolene (7.9 mg) was added to a test tube, the following solvents were added (cumulatively), and the drug did not dissolve: 0.3 ml mineral oil; +0.4 ml n-dibutyl ether; +0.4 ml methoxyflurane; +0.3 ml methoxyflurane; +0.3 ml methoxyflurane; +0.3 ml mineral oil. The above was sonicated with the microtip for 15 min. This resulted in a fine supension of dantrolene crystals which sedimented in about 15 min. The mixture was resonicated and 0.1 ml was removed and added to a test-tube containing 19.8 mg dilauryl phosphatidylcholine (lecithin). With swirling the lecithin was wetted but did not dissolve. Isotonic saline (1.5 ml) was added to the tube and the contents were sonicated. This resulted in a yellowish suspension of the consistency and appearance of egg nog. After two days storage the contents of the tube separated into three layers which were removed individually from the tube. The bottom layer had a volume of approx. 0.05 ml was a yellow-reddish mass which was easily resuspended in isotonic saline with gentle swirling. It contained the bulk of the dantrolene. It consisted of microcrystals of dantrolene wetted with the organic solvents and coated with a layer of lecithin. The middle layer, which represented the bulk of the volume, was very turbid. The top layer was lighter colored. The middle and top layers represented lecithin-coated microdroplets, as described by me in U.S. Pat. No. 4,725,442 (1988). The microdroplets in the middle layer were richer in methoxyflurane; the microdroplets in the top layer were richer in mineral oil. This example shows that if a stable, poorly-oil-soluble crystalline drug compound is selected, lecithin-coated microcrystals will spontaneously form during sonication, even when organic solvent is present in large quantities. This example provided insight into the physical interactions involved in the stability of the phospholipid-coated microcrystal.

EXAMPLE 15

This example shows how lecithin-coated microcrystal preparations of the anthelmintic drug albendazole can be diluted to give stable suspensions suitable for administration in drinking water for poultry and cattle. A concentrated preparation (20% (w/v) albendazole, (w/v) 10% lecithin) was made as described in Example 7. An aliquot was diluted into 400 ml of tap water to give a 0.25 mg/ml suspension which was stored without agitation in a capped 500 ml sample bottle. Immediately after dilution particle size analysis was performed. It showed 10% of the material in 254±200 nm particles, 85% in 2.7±0.5 um particles, and 5% in >3 um particles. After 64 hrs, only 45% of the drug had settled to the bottom third of the bottle. There was a thin translucent liquid film on the bottom. This was readily resuspended with a single inversion. Particle size analysis showed 54% of the material in 17±11 nm particles, 13% in 3.0±0.3 um particles, and 32% in >3 um particles. The test shows that the lecithin-coated microcrystal dispersed form is can be used in automatic dilution (proportionator) systems, even in cases where flow is interrupted for over 5 days.

EXAMPLE 16

This final example shows that the lecithin-coated microcrystal is a useful means of retarding the release of biomolecules after injection into tissue. Utility includes the sustained release of biologicals after depot injection and the prolonged retention of viral or bacterial antigen in the process of vaccination. Bovine serum albumin (BSA, 14-C labelled) was taken as an example of a water-soluble biomolecule. The BSA was admixed to a final concentration of 27 ug/ml with preformed oxytetracycline microcrystals (20% w/v OTC, 20% w/v) lecithin prepared as in Example 1. Laboratory rats were injected with 0.1 ml of the admixture (a) intradermally or (b) intramuscularly, and the skin and muscle injection sites were analyzed for 14-C BSA radioactivity remaining at sacrifice after two days. Controls were the same concentration of BSA in isotonic glucose solution and the same concentration of BSA admixed with lecithin vesicles (20% w/v) prepared by sonication. Table 6 shows that higher levels of 14-C BSA activity are found in skin and muscle sites for the lecithin-coated OTC microcrystal admixture.

TABLE 6

| Tissue/Trial | 14-C BSA Activity Remaining in Tissue 2 Days After Injection Glucose Soln | Lecithin Vesicles | OTC Microcrystals |
|---|---|---|---|
| Skin 1 | 5.0% | 3.0% | 88.0% |
| Skin 2 | 4.4% | 3.1% | 17.5% |
| Skin 3 | 4.2% | 3.9% | 12.6% |
| Muscle 1 | 5.9% | 0.0% | 27.8% |
| Muscle 2 | 8.6% | 8.2% | 6.2% |

These data suggest that the phospholipid-coated microcrystal can retain biologicals and antigens in its interstitial aqueous space, decreasing their rates of release from the injection site and thus prolonging their activity. The usefulness of the coated microcrystal for administration of biologicals or as a vaccine adjuvant (respectively) could be increased by including an immunosuppressant or immunostimulant drug (respectively) in the microcrystal.

What is claimed is:

1. A syringable, injectable pharmaceutical composition consisting essentially of an aqueous suspension of solid particles of a pharmacologically active water-insoluble drug substance in solid form, the solid particles having diameters of about 0.05 um to about 10 um, coated with a 0.3 nm to 3.0 um thick layer of a membrane-forming amphipathic lipid which stabilizes the drug substance from coalescence and renders the drug substance in solid form acceptable to tissue of host.

2. A syringable, injectable pharmaceutical composition consisting essentially of an aqueous suspension of crystals or solid particles of a pharmacologically active water-insoluble drug substance in solid form, the crystals or solid particles having diameters or maximal dimensions of about 0.05 um to about 10 um, coated with a 0.3 nm to 3.0 um thick encapsulating primary layer consisting of coating and enveloping layers of a membrane-forming amphipathic lipid, which stabilizes the drug substance from coalescence and renders the drug substance in solid form less irritating to living tissue, and 25 nm to 3.0 um thick secondary layer consisting of a membrane-forming amphipathic lipid in vesicular form associated with and surrounding but not enveloping the lipid-encapsulated drug particles, which composition is substantially devoid of uncoated crystals or particles.

3. The composition of claim 1 or claim 2, in which the drug substance particles have a diameter of about 0.1 um to about 3.2 um.

4. The composition of claims 1 or 2, in which a water-soluble drug is rendered water-insoluble by complexation with a pharmaceutically acceptable compound producing a crystalline or solid form.

5. The composition of claim 1 or 2, in which the weight ratio of drug to lipid is from about 1:1 to about 1,000:1.

6. The composition of claim 1 or 2, in which the membrane-forming lipid is a phospholipid.

7. The stable, syringable aqueous suspension of the composition of claim 1 or claim 2, containing by weight from 0.01 to about 40% of the drug substance.

8. The stable, syringable suspension of the composition of claim 1 or claim 2, dispersed in a pharmacologically acceptable, water-miscible polar organic liquid with a dielectric constant greater than 30, which polar organic liquid does not substantially dissolve the lipid membrane or membranes or the drug substance or a mixture of the polar organic liquid with water.

9. The composition of claim 2, in which the particles of drug substance are wetted with a water-immiscible oil of up to 0.25 gram per gram of drug substance, to facilitate contact between the drug crystals or particles and the primary layer of amphipathic membrane-forming lipid, or to slow the rate of drug dissolution or to otherwise modify the rate of drug release.

10. The composition of claim 2, in which the particles of drug substance are precoated by a layer of a waxy phospholipid-compatible solid having a melting point between 37° C. and 100° C. before or during the application of the primary layer of membrane-forming amphipathic lipid, the waxy phospholipid-compatible solid selected from paraffin, tristearin, ethyl oleate, cetostearyl alcohol, cetyl alcohol, myristyl alcohol, stearyl alcohol and petrolatum.

11. A solid pharmaceutical composition consisting essentially of the composition of claim 1 or claim 2, devoid of water which, when water is added, gives an aqueous suspension.

12. The pharmaceutical composition of claim 1 or claim 2 in injectable form for intravenous, intra-arterial, intra-muscular, intradermal, subcutaneous, intra-articular, cerebrospinal, epidural, intracostal, intraperitoneal, intratumor, intrabladder, intra lesional or subconjunctival administration.

13. The pharmaceutical composition of claim 1 or claim 2 in orally administrable form.

14. The pharmaceutical composition of claim 1 or claim 2 for topical application.

15. The pharmaceutical composition of claim 1 or claim 2 for inhalation.

16. The pharmaceutical composition of claim 1 or claim 2 for installation into the eye.

17. The pharmaceutical composition of claim 1 or claim 2 for dilution into drinking water.

18. The composition of claim 1 or claim 2 wherein the pharmacologically active water-soluble drug substance is a pesticide.

* * * * *